United States Patent
Chapman et al.

(10) Patent No.: US 12,350,506 B2
(45) Date of Patent: Jul. 8, 2025

(54) UP-TO-DATE DEFIBRILLATION RECOMMENDATIONS BASED ON CONTINUOUS ECG ANALYSIS DURING CARDIOPULMONARY RESUSCITATION

(71) Applicant: Stryker Corporation, Kalamazoo, MI (US)

(72) Inventors: Fred W. Chapman, Newcastle, WA (US); Steven Barry Duke, Bothell, WA (US); Robert P. Marx, Kent, WA (US); Daniel W Piraino, Seattle, WA (US); Tyson G. Taylor, Bothell, WA (US)

(73) Assignee: Stryker Corporation, Portage, MI (US)

( * ) Notice: Subject to any disclaimer, the term of this patent is extended or adjusted under 35 U.S.C. 154(b) by 375 days.

(21) Appl. No.: 17/559,992

(22) Filed: Dec. 22, 2021

(65) Prior Publication Data

US 2022/0193429 A1 Jun. 23, 2022

Related U.S. Application Data

(60) Provisional application No. 63/130,205, filed on Dec. 23, 2020.

(51) Int. Cl.
*A61N 1/39* (2006.01)
*G16H 20/30* (2018.01)
(Continued)

(52) U.S. Cl.
CPC ....... *A61N 1/3925* (2013.01); *A61N 1/39044* (2017.08); *A61N 1/3993* (2013.01);
(Continued)

(58) Field of Classification Search
CPC . A61N 1/3925; A61N 1/39044; A61N 1/3993
See application file for complete search history.

(56) References Cited

U.S. PATENT DOCUMENTS

| 5,687,735 A | 11/1997 | Forbes et al. |
| 5,853,364 A | 12/1998 | Baker, Jr. et al. |

(Continued)

FOREIGN PATENT DOCUMENTS

| EP | 2968965 B1 | 1/2016 |
| EP | 2295111 B1 | 7/2017 |

(Continued)

OTHER PUBLICATIONS

Aramendi, et al., "A Simple Effective Filtering Method for Removing CPR Caused Artefacts from Surface ECG Signals," Computers in Cardiology, Sep. 2005, pp. 547-550.

(Continued)

*Primary Examiner* — Tammie K Marlen
*Assistant Examiner* — Maria Catherine Anthony
(74) *Attorney, Agent, or Firm* — Lee & Hayes, P.C.

(57) ABSTRACT

Systems, devices, and methods provide up-to-date defibrillation shock recommendations. In an example method, multiple segments of an electrocardiogram (ECG) of an individual are detected from an individual receiving chest compressions. The multiple segments are evaluated to determine whether the individual is exhibiting a shockable heart rhythm. A medical device outputs a recommendation indicating whether a defibrillation shock is advised based on the most recent determination of the individual's heart rhythm. For example, the medical device outputs an up-to-date recommendation on-demand in response to an input signal from a user. In some examples, the medical device updates the recommendation based on ongoing analysis of the ECG.

20 Claims, 7 Drawing Sheets

(51) Int. Cl.
  *G16H 40/63* (2018.01)
  *G16H 50/30* (2018.01)
(52) U.S. Cl.
  CPC .............. *G16H 20/30* (2018.01); *G16H 40/63* (2018.01); *G16H 50/30* (2018.01)

(56) References Cited

U.S. PATENT DOCUMENTS

| | | | |
|---|---|---|---|
| 6,334,070 | B1 | 12/2001 | Nova et al. |
| 6,356,785 | B1 | 3/2002 | Snyder et al. |
| 6,752,771 | B2 | 6/2004 | Rothman et al. |
| 7,039,457 | B2 | 5/2006 | Young et al. |
| 7,220,235 | B2 | 5/2007 | Geheb et al. |
| 7,369,345 | B1 | 5/2008 | Li et al. |
| 7,565,194 | B2 | 7/2009 | Tan et al. |
| 7,567,837 | B2 | 7/2009 | Weil et al. |
| 7,650,181 | B2 | 1/2010 | Freeman et al. |
| 7,831,299 | B2 | 11/2010 | Tan et al. |
| 7,904,152 | B2 | 3/2011 | Sullivan et al. |
| 8,903,498 | B2 | 12/2014 | Sullivan et al. |
| 9,084,545 | B2 | 7/2015 | Sullivan et al. |
| 9,180,304 | B2 | 11/2015 | Quan et al. |
| 9,186,521 | B2 | 11/2015 | Quan et al. |
| 9,204,845 | B2 | 12/2015 | Sullivan et al. |
| 9,545,211 | B2 | 1/2017 | Sullivan et al. |
| 9,642,575 | B2 | 5/2017 | Freeman et al. |
| 9,751,534 | B2 | 9/2017 | Fung et al. |
| 9,801,561 | B2 | 10/2017 | Sullivan et al. |
| 9,919,160 | B2 | 3/2018 | Firoozabadi et al. |
| 10,080,904 | B2 | 9/2018 | Sullivan |
| 10,117,804 | B2 | 11/2018 | Nilsson et al. |
| 10,155,120 | B2 | 12/2018 | Zaidi et al. |
| 10,258,248 | B2 | 4/2019 | Quan et al. |
| 10,905,344 | B2 | 2/2021 | Sullivan et al. |
| 2002/0165471 | A1 | 11/2002 | Halperin et al. |
| 2005/0101889 | A1 | 5/2005 | Freeman et al. |
| 2005/0137628 | A1 | 6/2005 | Young et al. |
| 2005/0256415 | A1 | 11/2005 | Tan et al. |
| 2006/0025824 | A1 | 2/2006 | Freeman et al. |
| 2006/0149157 | A1 | 7/2006 | Weil et al. |
| 2006/0235320 | A1 | 10/2006 | Tan et al. |
| 2006/0258927 | A1 | 11/2006 | Edgar, Jr. et al. |
| 2007/0100379 | A1 | 5/2007 | Tan et al. |
| 2007/0142735 | A1 | 6/2007 | Shin et al. |
| 2007/0162076 | A1 | 7/2007 | Tan et al. |
| 2009/0204162 | A1 | 8/2009 | Addison et al. |
| 2010/0016685 | A1 | 1/2010 | Muehlsteff et al. |
| 2010/0076510 | A1 | 3/2010 | Lyster |
| 2011/0034816 | A1 | 2/2011 | Tan et al. |
| 2011/0082510 | A1 | 4/2011 | Sullivan |
| 2011/0105930 | A1 | 5/2011 | Thiagarajan et al. |
| 2011/0144707 | A1 | 6/2011 | Sullivan et al. |
| 2011/0202100 | A1 | 8/2011 | Tan et al. |
| 2011/0202101 | A1 | 8/2011 | Tan et al. |
| 2012/0010543 | A1* | 1/2012 | Johnson ................ G16H 20/40 601/41 |
| 2012/0016279 | A1 | 1/2012 | Banville et al. |
| 2012/0157865 | A1 | 6/2012 | Stein et al. |
| 2013/0184600 | A1 | 7/2013 | Tan et al. |
| 2014/0088374 | A1 | 3/2014 | Sullivan et al. |
| 2014/0100497 | A1 | 4/2014 | Hayashi et al. |
| 2014/0243915 | A1 | 8/2014 | Freeman et al. |
| 2015/0297107 | A1 | 10/2015 | Sullivan et al. |
| 2015/0352367 | A1* | 12/2015 | Quan .................... A61B 5/7253 601/41 |
| 2016/0008613 | A1 | 1/2016 | Snyder |
| 2016/0220833 | A1 | 8/2016 | Tan et al. |
| 2016/0279405 | A1 | 9/2016 | Riley et al. |
| 2017/0105644 | A1 | 4/2017 | Sullivan et al. |
| 2017/0361120 | A1 | 12/2017 | Liu et al. |
| 2018/0303367 | A1 | 10/2018 | Sullivan et al. |
| 2019/0059745 | A1 | 2/2019 | Tan et al. |
| 2019/0374428 | A1* | 12/2019 | Kaufman ........... A61N 1/39044 |
| 2020/0253495 | A1 | 8/2020 | Tan et al. |
| 2021/0015387 | A1 | 1/2021 | Sullivan et al. |
| 2021/0030294 | A9 | 2/2021 | Sullivan et al. |
| 2022/0193430 | A1 | 6/2022 | Chapman et al. |
| 2022/0193431 | A1 | 6/2022 | Chapman et al. |
| 2022/0193433 | A1 | 6/2022 | Chapman et al. |

FOREIGN PATENT DOCUMENTS

| | | |
|---|---|---|
| JP | 4890687 B2 | 3/2012 |
| JP | 6090776 B2 | 3/2017 |
| WO | WO2009071128 A1 | 6/2009 |

OTHER PUBLICATIONS

Aramendi, et al., "Detection of ventricular fibrillation in the presence of cardiopulmonary resuscitation artefacts," Resuscitation (2007) 72, Jan. 2007, pp. 115-123.

Aramendi, et al., "Suppression of the cardiopulmonary resuscitation artefacts using the instantaneous chest compression rate extracted from the thoracic impedance," Resuscitation 83 (2012), Jun. 2012, pp. 692-698.

Berger, et al., "Rhythm discrimination during uninterrupted CPR using motion artifact reduction system," Resuscitation (2007) 75, Oct. 2007, pp. 145-152.

Dotsinsky, et al., "Fast Electrocardiogram Amplifier Recovery after Defibrillation Shock," Bioautomation (2005) 2, Apr. 2005, pp. 76-84.

Dotsinsky, "Suppression of AC railway power-line interference in ECG signals recorded by public access defibrillators," BioMedical Engineering OnLine (2005) 4:65, Nov. 2005, 8 pages.

Extended European Search Report, mailed Mar. 1, 2017, EP Application No. 16178129.9, filed Jul. 6, 2016, 17 pages.

Granegger, et al., "Use of independent component analysis for reducing CPR artefacts in human emergency ECGs," Resuscitation (2011) 82(1), Jan. 2011, pp. 79-84.

Irusta, et al., "A Least Mean Square Filter for the Estimation of the Cardiopulmonary Resuscitation Artifact Based on the Frequency of the Compressions," IEEE Transaction on Biomedical Engineering (2009) 56:(4), Apr. 2009, pp. 1052-1062.

International Search Report and Written Opinion for PCT/US13/39555, mailed on Oct. 1, 2013, 22 pages.

Lee, et al., "Adaptive Comb Filtering for Motion Artifact Reduction from PPG with a Structure of Adaptive Lattice IIR Notch Filter," 33rd Annual International Conference of the IEEE EMBS, Boston, MA, Aug. 30-Sep. 3, 2011, pp. 7937-7940.

Office Action for U.S. Appl. No. 14/656,666, mailed on Jan. 25, 2016, Sullivan, "System and Method for Electrocardiogram Analysis and Optimization of Cardiopulmonary Resuscitation and Therapy Delivery," 11 pages.

Office Action for U.S. Appl. No. 13/836,062, mailed on Jan. 31, 2014, Sullivan, "System and Method for Electrocardiogram Analysis and Optimization of Cardiopulmonary Resuscitation and Therapy Delivery", 4 pages.

Office Action for U.S. Appl. No. 13/676,593, mailed on Nov. 26, 2014, Sullivan, "Filter Mechanism for Removing ECG Artifact From Mechanical Chest Compressions", 6 pages.

Office Action for U.S. Appl. No. 15/796,575, mailed on Dec. 26, 2019, Sullivan, "System and Method for Electrocardiogram Analysis and Optimization of Cardiopulmonary Resuscitation and Therapy Delivery", 7 pages.

Office Action for U.S. Appl. No. 13/676,593, mailed on Feb. 7, 2014, Sullivan, "Filter Mechanism for Removing ECG Artifact From Mechanical Chest Compressions", 12 pages.

Office Action for U.S. Appl. No. 15/395,780, mailed on Mar. 8, 2017, Sullivan, "System and Method for Electrocardiogram Analysis and Optimization of Cardiopulmonary Resuscitation and Therapy Delivery," 6 pages.

Office Action for U.S. Appl. No. 15/796,575, mailed on Apr. 1, 2019, Sullivan, "System and Method for Electrocardiogram Analysis and Optimization of Cardiopulmonary Resuscitation and Therapy Delivery", 7 pages.

(56) References Cited

OTHER PUBLICATIONS

Office Action for U.S. Appl. No. 14/558,610, mailed on May 12, 2015, Sullivan, "System and Method for Electrocardiogram Analysis and Optimization of Cardiopulmonary Resuscitation and Therapy Delivery", 10 pages.

Office Action for U.S. Appl. No. 14/656,666, mailed on May 25, 2016, Sullivan, "System and Method for Electrocardiogram Analysis and Optimization of Cardiopulmonary Resuscitation and Therapy Delivery," 9 pages.

Office Action for U.S. Appl. No. 13/676,593, mailed on Jun. 11, 2014, Sullivan, "Filter Mechanism for Removing ECG Artifact From Mechanical Chest Compressions", 10 pages.

Office Action for U.S. Appl. No. 15/796,575, mailed on Aug. 29, 2019, Sullivan, "System and Method for Electrocardiogram Analysis and Optimization of Cardiopulmonary Resuscitation and Therapy Delivery", 6 pages.

Ruiz de Gauna, et al., "A method to remove CPR artefacts from human ECG using only the recorded ECG," Resuscitation (2008) 76(2), Feb. 2008, pp. 271-278.

Ruiz, et al., "Cardiopulmonary resuscitation artefact suppression using a Kalman filter and the frequency of chest compressions as the reference signal," Resuscitation (2010) 81(9), Sep. 2010, pp. 1087-1094.

Office Action for U.S. Appl. No. 17/559,925, mailed on Mar. 26, 2024, Chapman, "Defibrillators With Enhanced Functionality During Cardiopulmonary Resuscitation Periods", 7 pages.

Office Action for U.S. Appl. No. 17/559,795, mailed on Mar. 28, 2024, Chapman, "Detecting and Addressing Irregular Motion to Improve Defibrillation Shock Recommendations", 25 pages.

Office Action for U.S. Appl. No. 17/560,043, mailed on Jul. 3, 2024, Chapman, "Enhanced Defibrillation Shock Decisions", 28 pages.

Office Action for U.S. Appl. No. 17/559,795, mailed on Dec. 11, 2024, Chapman, "Detecting and Addressing Irregular Motion to Improve Defibrillation Shock Recommendations", 33 pages.

Porciuncula, et al., "Wearable Movement Sensors for Rehabilitation: A Focused Review of Technological and Clinical Advances", HHS Public Access, PM&R. Sep. 2018; 10(9 Suppl 2):S220-S232. doi: 10.1016/j.pmrj.2018.06.013, 2019, 21 pages.

Office Action for U.S. Appl. No. 17/559,925, mailed on Oct. 16, 2024, Chapman, "Defibrillators With Enhanced Functionality During Cardiopulmonary Resuscitation Periods", 8 pages.

* cited by examiner

UP-TO-DATE DEFIBRILLATION RECOMMENDATIONS BASED ON CONTINUOUS ECG ANALYSIS DURING CARDIOPULMONARY RESUSCITATION

CROSS-REFERENCE TO RELATED APPLICATION

This application claims the priority of U.S. Provisional Application No. 63/130,205, titled "UP-TO-DATE DEFIBRILLATION RECOMMENDATIONS BASED ON CONTINUOUS ECG ANALYSIS DURING CARDIOPULMONARY RESUSCITATION," which was filed on Dec. 23, 2020 and is incorporated by reference herein in its entirety.

BACKGROUND

Cardiac arrest is a condition in which an individual's heart ceases to function effectively. During cardiac arrest, the brain and other vital organs are unable to receive sufficient oxygenated blood, which can result in a sudden loss of consciousness. If untreated shortly after onset, cardiac arrest is deadly. Thus, effective treatments must be applicable in a variety of environments where cardiac arrest is likely to occur, such as environments outside of hospitals or other specialized facilities for administering medical care.

Cardiopulmonary resuscitation (CPR) is a treatment that forces blood to vital organs using chest compressions, which can be administered manually or via a chest compression device. CPR is indicated for individuals experiencing cardiac arrest and can slow down damage to the vital organs by providing at least some blood flow despite the heart's disfunction. However, the underlying cause of the cardiac arrest is not treatable by CPR.

Some forms of cardiac arrest are the result of abnormal heart rhythms, such as ventricular fibrillation (VF) and pulseless ventricular tachycardia (V-tach). VF and pulseless V-tach are treatable by defibrillation, which is the delivery of an electrical shock to the heart. Because a defibrillation shock can be dangerous if administered to individuals without VF or pulseless V-tach, a defibrillator will generally identify and/or assist in the diagnosis of VF and pulseless V-tach based on electrocardiograms (ECGs). An ECG includes signals from one or more leads that are indicative of the electrical activity of an individual's heart over time.

DETAILED DESCRIPTION

Figure 1:
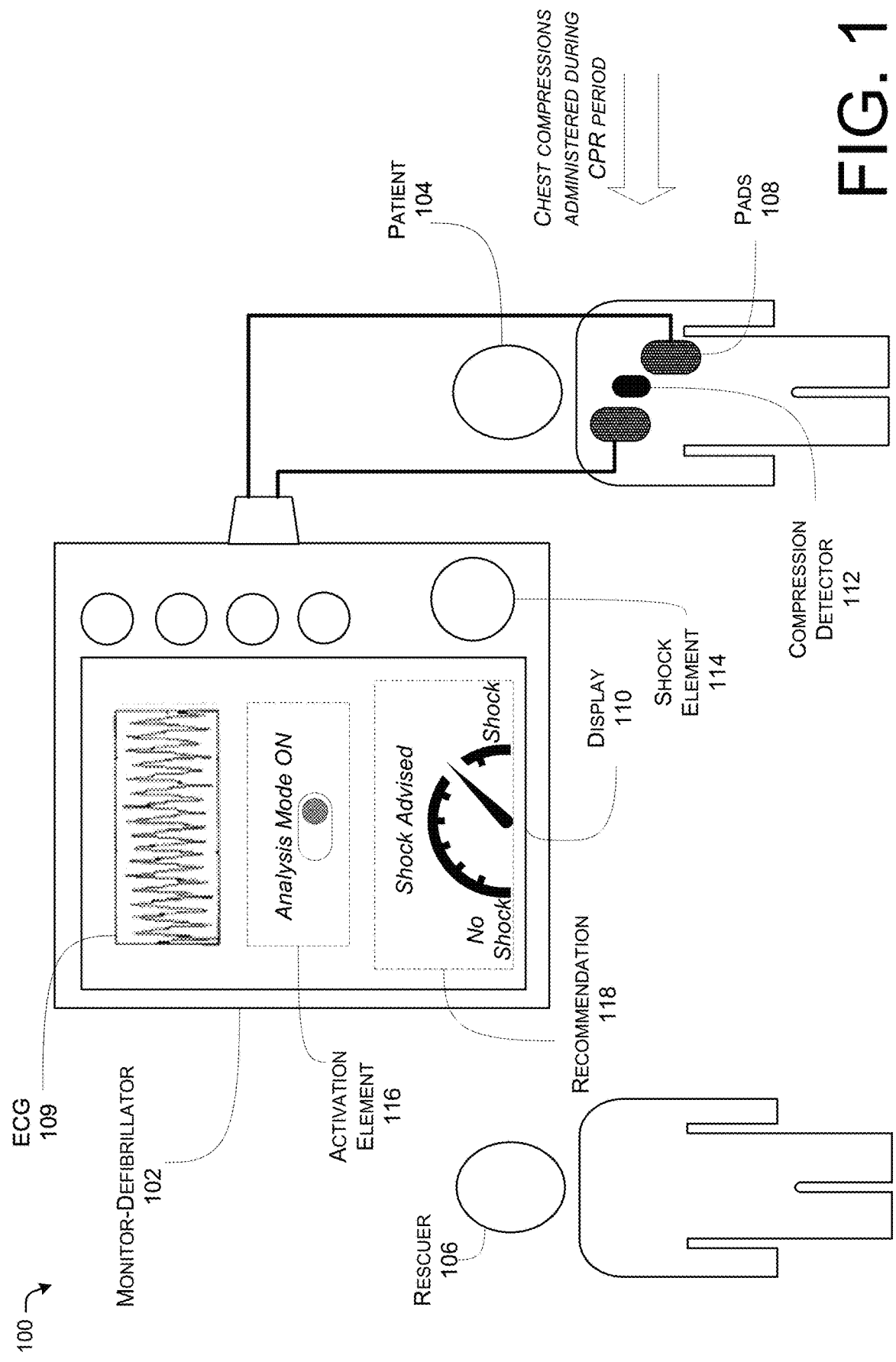
FIG. 1 illustrates an example emergency environment including a monitor-defibrillator that periodically or repeatedly analyzes a heart rhythm of a patient as the patient is receiving chest compressions.

Various implementations described herein relate to systems, devices, and methods for outputting on-demand recommendations for whether to treat an individual with a defibrillation shock following a CPR period wherein the analysis to inform the recommendation is performed while the individual is receiving chest compressions during the CPR period. For example, a device automatically runs a continuous or repeated analysis on an ECG of the individual in order to determine whether the individual is experiencing a shockable heart rhythm (e.g., VF or pulseless V-Tach). In various cases, the device selectively outputs a recommendation based on the most recently-completed analysis in response to a user input. Because the device has already analyzed the ECG prior to the user input, the user does not have to wait for the device to analyze the ECG when the user requests the recommendation from the device.

Various implementations described herein relate to systems, devices, and methods for continuously or repeatedly analyzing an ECG of an individual receiving chest compressions, and updating a recommendation indicating whether to administer a defibrillation shock to the individual. In some cases, the recommendation is updated based on the continuous or repeated ECG analyses. In various examples, the recommendation also includes a real-time estimate of the certainty that the recommendation is correct and/or that the individual is exhibiting a shockable heart rhythm. Accordingly, a user can monitor the condition of the individual, and make an informed decision about applying the defibrillation shock, substantially in real-time.

Implementations described herein solve specific problems in the technical field of medical devices. In emergency scenarios, delays to administering life-saving therapies like defibrillation can have serious consequences. For instance, a heart in VF is unable to adequately oxygenate the brain and other vital organs. Although CPR can reduce the damage of cardiac arrest by providing some perfusion of blood to the body, the brain and other vital organs are still in danger of long-term damage while the individual remains in cardiac arrest. Thus, reducing the time to treat the arrhythmia can greatly improve health outcomes of individuals in cardiac arrest.

In some examples of the present disclosure, a medical device outputs a recommendation of whether to administer a defibrillation shock immediately after the device receives an input signal (e.g., from a rescuer) requesting the recommendation. The medical device generates and/or updates the recommendation, in advance of receiving the input signal. Thus, the output of the recommendation is not delayed by the time it would otherwise take the medical device to analyze the ECG. By outputting the recommendation quickly and on-demand, the medical device can reduce the time that a rescuer takes to treat a potentially shockable arrhythmia of the individual.

The chest compressions applied to the individual can make it difficult to assess whether the individual is exhibiting the arrhythmia. For example, the chest compressions generate a significant artifact in the individual's ECG, which can interfere with a rescuer's ability to assess whether a shockable rhythm is present in the ECG. Various implementations described herein relate to devices, systems, and methods for generating a filtered ECG segment by removing at least a portion of the artifact from a segment of the ECG and analyzing the filtered ECG segment for a shockable rhythm. Thus, the recommendation is output as chest compressions are administered to the individual, for example.

Discrete segments of the ECG are analyzed for the shockable rhythm, in various examples. However, the individual's heart rhythm can change over time. For example, an earlier segment of the ECG indicates that the individual is exhibiting a shockable rhythm, but a later segment of the ECG indicates that the individual is exhibiting a nonshockable rhythm (e.g., asystole). In some cases, a medical device performs the analysis repeatedly and/or periodically, based on segments of the ECG as they are detected from the individual. The medical device outputs a recommendation indicating whether a defibrillation shock is indicated for the individual. The medical device updates the recommendation as the medical device determines whether recent segments of the ECG exhibit the shockable rhythm. In some examples, the recommendation is further updated with a certainty of whether the defibrillation shock is indicated. Various implementations described herein can be used for manually operated defibrillation devices, such as monitor-defibrillators operating in manual mode. For example, the medical device continues to analyze new segments of the ECG for the shockable rhythm even after the medical device determines that an earlier segment exhibited the shockable rhythm. Various examples described herein improve the operation of defibrillators by providing rescuers and other users with accurate, up-to-date recommendations about the heart rhythm of the individual being treated, even as CPR is being administered to the individual.

Particular examples will now be described with reference to the accompanying figures. The scope of this disclosure includes individual examples described herein as well as any combination of the examples, unless otherwise specified.

FIG. 1 illustrates an example emergency environment 100 including a monitor-defibrillator 102 that repeatedly or periodically analyzes a heart rhythm of a patient 104 as the patient 104 is receiving chest compressions. The patient 104 is experiencing cardiac arrest, for example. In the example environment 100 of FIG. 1, the monitor-defibrillator 102 is operated by a rescuer 106. In some implementations, the rescuer 106 has at least some medical training and is a trained operator of the monitor-defibrillator 102. For example, the rescuer 106 is an emergency responder, a physician, a nurse, or the like. In particular examples, the rescuer 106 is an untrained user and the monitor-defibrillator 102 operates as an automated external defibrillator (AED).

The monitor-defibrillator 102 includes pads 108 that are disposed on the patient 104. The pads 108 include multiple electrodes that are in contact with the patient 104. In some examples, the pads 108 are adhered to the skin of the patient 104. For example, the pads 108 are adhered to the skin of the patient 104 by a biocompatible adhesive. In various cases, the pads 108 include a substrate (e.g., a flexible substrate) that is adhered to the skin of the patient 104 by an adhesive.

The pads 108, for example, include electrodes (e.g., therapeutic electrodes) that are in contact with the patient 102. The monitor-defibrillator 102 is an external defibrillator, for instance, such that the electrodes are in contact with the skin of the patient 102. The pads 108, for example, include two electrodes, three electrodes, ten electrodes, or twelve electrodes. The electrodes receive an electrical signal indicative of an electrical activity of the heart of the patient 102. For example, the heart of the patient 102 outputs an electrical field that impacts the relative voltages between the electrodes.

The pads 108 are connected to additional circuitry in the monitor-defibrillator 102 by connectors. The connectors are wired connections, wireless connections, or a combination thereof. In various examples, the monitor-defibrillator 102 includes a detection circuit configured to detect an ECG 109 of the patient 104 based on the voltages between the therapeutic electrodes. In some cases, the detection circuit includes an analog to digital converter that converts the relative voltages (representing the ECG 109 in an analog form) into digital data (representing the ECG 109 in a digital format). Although the ECG 109 pictured in FIG. 1 depicts a single waveform corresponding to a single (lead) voltage between two therapeutic electrodes, implementations of the present disclosure are not so limited.

The monitor-defibrillator 102 includes a display 110 that is configured to visually output information to the rescuer 106. In some examples, the display 110 includes a touchscreen configured to receive touch signals from the rescuer 106. These touch signals are examples of input signals that the monitor-defibrillator 102 receives from the rescuer 106. In various cases, the monitor-defibrillator 102 includes other types of input devices configured to receive input signals, such as buttons, knobs, microphones, tactile devices, and the like. For instance, the monitor-defibrillator 102 may analyze the ECG 109 based on the microphone receiving a verbal "analyze" command. In various examples, the monitor-defibrillator 102 outputs the ECG 109 on the display 110. The rescuer 106, for instance, can assess a condition of the patient 104 based on the displayed ECG 109. In some examples, the rescuer 106 determines whether the ECG 109 exhibits a shockable rhythm, such as VF or pulseless V-Tach. If the shockable rhythm is present in the ECG 109, in some examples, the rescuer 106 treats the shockable rhythm by causing the monitor-defibrillator 102 to administer a defibrillation shock to the patient 104.

However, as shown in FIG. 1, the monitor-defibrillator 102 detects the ECG 109 from the pads 108 as chest compressions are administered to the patient 104. The chest compressions are administered manually (e.g., by the rescuer) or by a chest compression device, such as LUCAS®, by Stryker Corporation of Kalamazoo, Mich. The chest compressions impart a significant artifact in the ECG 109. For example, the physical interface between the detection electrodes and the skin of the patient 104 are jostled by the chest compressions, the user or device administering the chest compressions impacts the voltage received by the detection electrodes, or a combination thereof. Due to the chest compression artifact (also referred to as a "compression artifact") in the ECG 109, the rescuer 106 may be unable to accurately discern whether the patient 104 is exhibiting the shockable rhythm.

In various implementations, the monitor-defibrillator 102 analyzes the ECG 109 in order to determine whether the shockable rhythm is present. For example, the monitor-defibrillator 102 generates a processed ECG segment (e.g., a filtered ECG segment) by removing at least a portion of the chest compression artifact from a segment of the ECG 109. The segment has a time period that is greater than or equal to 3 seconds and less than or equal to 30 seconds, for instance. In some examples, the monitor-defibrillator 102 generates a processed ECG by removing at least a portion of the chest compression artifact from samples of the ECG 109, wherein the samples are separated in the time domain by a time interval that is greater than the sampling period of the ECG 109. In various examples, the monitor-defibrillator 102 removes at least the portion of the chest compression artifact by applying an adaptive filter (e.g., a Wiener filter, a Kalman filter, or the like), applying a comb filter, applying an inverse comb filter, applying a high-pass filter, applying a band reject filter, applying a finite impulse response (FIR) filter, applying an infinite impulse response (IIR) filter, identifying and subtracting the chest compression artifact, or a combination thereof. In some cases, the monitor-defibrillator 102 converts the ECG 109 from the time domain into the frequency (e.g., a Fourier) domain, a Laplace domain, a Z-transform domain, or a wavelet (e.g., a continuous wavelet transform, a discrete wavelet transform, etc.) domain, and removes the chest compression artifact by analyzing the converted ECG 109. Although this disclosure specifically describes various techniques for generating the processed ECG segment, other techniques known in the art of signal processing can be used to generate the processed ECG segment. Furthermore, in some cases, the monitor-defibrillator 102 generates the processed ECG segment by transforming a segment of the ECG 109 into a format that reduces or eliminates the impact of the chest compression artifact on the transformed ECG. For instance, the monitor-defibrillator 102 applies a transformation that floats the artifact away from the ECG 109 onto another abstract signal, which can be ignored by the monitor-defibrillator 102 in future processing.

In some implementations, the monitor-defibrillator 102 identifies the chest compression artifact by detecting the chest compressions administered to the patient 104. For instance, the monitor-defibrillator 102 determines a component of the ECG segment that corresponds to the chest compressions (e.g., in the frequency domain). Because the chest compression artifact is corresponded with the chest compressions administered to the patient 104, the monitor-defibrillator 102 identifies and removes the chest compression artifact based on the chest compressions, for example.

According to some instances, the monitor-defibrillator 102 detects the chest compressions administered to the patient 104 by detecting an electrical impedance between the detection electrodes in the pads 108. This electrical impedance can be referred to as an electrical impedance of the patient 104, in some implementations. For example, the monitor-defibrillator 102 outputs a voltage across at least one detection electrode in a first one of the pads 108 and at least one detection electrode in a second one of the pads 108, detects a current at one of the detection electrodes, and determines the impedance of the patient 104 based on the voltage and the current (e.g., by dividing the voltage by the current). In various examples, there is a time delay between the voltage and the current, and the impedance of the patient 104 is determined based on the voltage, the current, and the delay (e.g., dividing the voltage by the current while accounting for the delay). The impedance of the patient 104 changes over time based on the chest compressions administered to the patient 104. Thus, in some cases, the monitor-defibrillator 102 detects the chest compressions based on a waveform of the impedance of the patient 104 over time.

In some examples, the monitor-defibrillator 102 detects the chest compressions based on a compression detector 112 disposed on the patient 104. In various examples, the compression detector 112 generates a signal indicative of the chest compressions applied to the patient 104. In some instances, the compression detector 112 includes an accelerometer, a gyroscope, a pressure sensor, or any combination thereof. In some examples, the compression detector 112 detects the chest compressions via positions between multiple radio frequency identification (RFID) tags within the compression detector 112, a change in a magnetic field within the compression detector, a mechanical lever within the compression detector 112, processing of images captured by a camera within the compression detector, or the like. The compression detector 112 transmits the signal that is indicative of the chest compression to the monitor-defibrillator 102 over a wired and/or wireless connection. In some implementations, the compression detector 112 generates multiple signals indicative of the chest compressions over time and transmits the signals to the monitor-defibrillator 102 (e.g., periodically), such that the monitor-defibrillator 102 detects the chest compressions substantially in real-time.

The monitor-defibrillator 102 generates a shock index based on the filtered ECG segment. In various examples, the shock index corresponds to a likelihood and/or certainty that the filtered ECG segment includes the shockable rhythm and/or that the patient 104 exhibits the shockable rhythm during the time period corresponding to the segment of the ECG. In some cases, the monitor-defibrillator 102 determines whether the shockable rhythm is present in the filtered ECG segment by comparing the shock index to a threshold. For example, the monitor-defibrillator 102 determines that the shockable rhythm is present (e.g., a "shockable" decision) if the shock index is greater than a first threshold and a second threshold, that the shockable rhythm is absent (e.g., a "nonshockable" decision) if the shock index is less than the first threshold and the second threshold, and that it is unclear whether the shockable rhythm is present (e.g., an "indeterminate" decision) if the shock index is greater than the first threshold and less than the second threshold.

In various cases, the monitor-defibrillator 102 is operating in an automatic mode. In the automatic mode, the monitor-defibrillator 102 automatically begins to charge (e.g., the monitor-defibrillator 102 charges a capacitor) in response to detecting the shockable rhythm. The monitor-defibrillator 102, in some cases, automatically administers a defibrillation shock after being charged. Thus, in the automatic mode, the monitor-defibrillator 102 automatically treats the patient 104 with a defibrillation shock when the patient 104 is exhibiting a shockable rhythm.

In various implementations of the present disclosure, the monitor-defibrillator 102 is operating in a manual mode. In the manual mode, the monitor-defibrillator 102 is configured to administer a defibrillation shock in response to direction by the rescuer 106. For instance, the monitor-defibrillator 102 administers the defibrillation shock based on a shock element 114 receiving an input signal. The shock element 114 is, for example, includes a button, a dial, a switch, or any other input device configured to receive an input signal from a user, such as the rescuer 106. In some cases, the monitor-defibrillator 102 charges in response to direction by the rescuer 106. The monitor-defibrillator 102, for example, refrains from charging and/or administering the defibrillation shock unless the monitor-defibrillator 102 receives an appropriate input signal from the rescuer 106 or another user. In the manual mode, the condition is diagnosed and treated by the rescuer 106.

In the manual mode, however, the rescuer 106 may want the benefit of an assessment by the monitor-defibrillator 102. In some examples, the monitor-defibrillator 102 activates an advisory mode when the rescuer 106 interacts with an activation element 116. In the example of FIG. 1, the activation element 116 is a user interface element of the monitor-defibrillator 102. For instance, the monitor-defibrillator 102 displays a graphical user interface (GUI) element corresponding to the activation element 116 on the display 110. In cases wherein the display 110 is a touchscreen, the monitor-defibrillator 102 activates the advisory mode based on an input signal received by one or more touch sensors associated with an area corresponding to the GUI element of the activation element 116. For instance, the monitor-defibrillator 102 activates the advisory mode based on the rescuer 106 touching a GUI button or sliding a GUI element output by the touchscreen. In some cases, the monitor-defibrillator 102 activates the advisory mode based on the microphone of the monitor-defibrillator 102 receiving an audio command, such as a particular word or phrase (e.g., "activate advisory mode"). The monitor-defibrillator 102, for instance, includes software and/or hardware configured to perform speech recognition on an audio signal received by the microphone and to identify the command based on the speech recognition.

Based on the input signal received by the monitor-defibrillator 102 at the activation element 116 or some other input device, the monitor-defibrillator 102 outputs a recommendation 118. The recommendation 118 includes an indication of a shock decision determined by the monitor-defibrillator 102. For example, in the example of FIG. 1, the monitor-defibrillator 102 determines that a segment of the ECG 109 includes a shockable rhythm and outputs the recommendation 118 to indicate that treating the patient 104 with a defibrillation shock is advised. If, however, the monitor-defibrillator 102 were to determine that the shockable rhythm was absent from the segment of the ECG 109, the monitor-defibrillator 102 would output the recommendation 118 to indicate that treating the patient 104 with a defibrillation shock is not advised. In cases where the monitor-defibrillator 102 comes to an indeterminate decision about the segment of the ECG 109, the monitor-defibrillator 102 outputs the recommendation 118 to indicate that the monitor-defibrillator 102 was unable to determine whether the segment of the ECG 109 included the shockable rhythm (e.g., to a sufficient level of certainty) and/or that chest compressions should be paused to facilitate further analysis of the ECG 109. For instance, if the chest compressions are paused, the monitor-defibrillator 102 may evaluate a segment of the ECG 109 without a chest compression artifact, thereby increasing the certainty that the monitor-defibrillator 102 identifies a shockable or nonshockable rhythm in the ECG 109.

In some examples, the recommendation 118 further indicates the certainty of the shock decision (e.g., shockable, nonshockable, or indeterminate) in the recommendation 118. The monitor-defibrillator 102 determines the certainty based on the shock index, in some cases. In FIG. 1, the certainty is indicated by a gauge GUI element. An arm of the gauge points to a scale of the gauge that indicates the certainty of the shock decision. For example, if the arm is pointed to a rightmost side of the scale, the gauge indicates that the monitor-defibrillator 102 is very certain (e.g., 100% certain) that the shockable rhythm is present in the ECG 109 and the shock decision is a shockable decision. In instances wherein the arm is pointed to a leftmost side of the scale, the gauge indicates that the monitor-defibrillator 102 is very certain (e.g., 100% certain) that the shockable rhythm is absent from the ECG 109 and that the shock decision is a nonshockable decision. In the example illustrated in FIG. 1, the gauge indicates that the monitor-defibrillator 102 is moderately certain that the shockable rhythm is present in the ECG 109. In some cases, the recommendation 118 displays the certainty of the shock decision as a percentage certainty, a color of the recommendation 118 (e.g., green for greater than a first threshold certainty that the shockable rhythm is present, yellow for less than the first threshold certainty that the shockable rhythm is present and less than a second threshold certainty that a shockable rhythm is present, red for greater than the second threshold certainty that a nonshockable rhythm is present in the ECG 109), or as any other visual indicator of certainty.

In some cases, the monitor-defibrillator 102 outputs the recommendation 118 as an audio signal. For example, the monitor-defibrillator 102 includes a speaker that outputs a first sound when the monitor-defibrillator 102 determines the shockable rhythm is present in the ECG 109 at greater than a threshold certainty, a second sound when the monitor-defibrillator 102 determines that the shockable rhythm is absent in the ECG 109 at greater than a threshold certainty, and a third sound when the monitor-defibrillator 102 is unable to determine whether the shockable rhythm is present and/or absent to a threshold certainty. In some cases, the audio signal output by the monitor-defibrillator 102 indicates the certainty that the shockable rhythm is present in the ECG 109. In particular examples, the speaker outputs an audio signal including the phrase "consider shock," "shock advised," "shock highly advised," "30% probability of shockable rhythm," "70% probability of nonshockable rhythm," or the like.

Because the monitor-defibrillator 102 generates the recommendation 118 based on a discrete segment of the ECG 109, there is a delay between the time that the monitor-defibrillator 102 begins to obtain the segment being analyzed and the time that the monitor-defibrillator 102 generates the recommendation 118. In some examples described herein, the monitor-defibrillator 102 waits to generate the recommendation 118 until the analysis mode is activated. In some examples, this can reduce the processing load on the monitor-defibrillator.

However, in some cases, if the monitor-defibrillator 102 waits until the analysis mode is activated to analyze the ECG 109, the rescuer 106 experiences a delay between the time that the analysis mode is activated and the monitor-defibrillator 106 outputs the recommendation 118. This delay can lengthen the time that the rescuer 106 takes to treat the patient 104.

To avoid and/or reduce this delay, the monitor-defibrillator 102 analyzes the ECG 109 before the analysis mode is activated in some implementations. The monitor-defibrillator 102 periodically and/or repeatedly analyses discrete segments of the ECG 109 and determines shock decisions based on the discrete segments. When the monitor-defibrillator 102 receives the input signal that activates the analysis mode, the monitor-defibrillator 102 retrieves the most recent, already-determined shock decision and immediately outputs the recommendation 118 based on the retrieved shock decision or outputs the decision without significant delay (e.g., within 5 seconds, 4 seconds, 3 seconds, 2 seconds, or 1 second). Thus, the monitor-defibrillator 102 provides the recommendation 118 on-demand to the rescuer 106, even when the patient 104 is receiving chest compressions.

Furthermore, when the analysis mode is activated, the monitor-defibrillator 102 continues to analyze segments of the ECG 109 as they are detected by the monitor-defibrillator 102. The monitor-defibrillator 102 updates the recommendation 118 with a new determined shock decision and/or a new determined shock decision certainty. For instance, the monitor-defibrillator 102 updates the recommendation with every one, every second, every third, every fourth, or every fifth newly determined shock decision and/or certainty. Thus, if the heart rhythm of the patient 104 changes over time, the monitor-defibrillator 102 identifies and reports the changing shockable decision and/or changing heart rhythm to the rescuer 106. For example, the monitor-defibrillator 102 determines that the patient 104 initially exhibits VF and outputs the recommendation 118 to indicate that a shock is advised, but then determines that the VF has resolved and updates the recommendation 118 to indicate that the shock is no longer advised.

In some cases, whether the analysis mode is active or inactive, the monitor-defibrillator 102 continuously analyzes the ECG 109 by repeatedly and/or periodically analyzing segments of the ECG 109. For example, the monitor-defibrillator 102 repeatedly analyzes the ECG 109 by analyzing non-overlapping segments of the ECG 109. In some cases, the start time of one segment is simultaneous with or after the end time of another segment that is analyzed. In some cases, the monitor-defibrillator 102 analyzes a segment in response to generating a shock decision about a previous segment. In implementations in which the monitor-defibrillator 102 periodically analyzes segments of the ECG 109, the start times of the segments are separated by a particular time period. In some examples, the segments overlap. In various implementations, the monitor-defibrillator 102 analyzes multiple segments of the ECG 109 simultaneously. The monitor-defibrillator 102, in some examples, performs multiple parallel analyses of the multiple segments. By continuously analyzing segments of the ECG 109, the monitor-defibrillator 102 is ready to output the recommendation 118 immediately after the analysis mode is activated. Furthermore, by continuously analyzing segments of the ECG 109, the monitor-defibrillator 102 updates the recommendation 118 to reflect an accurate shock decision substantially in real-time, or near real time.

In some implementations, the monitor-defibrillator 102 averages or otherwise combines shock indices generated based on multiple segments of the ECG 109, and generates the recommendation 118 based on the average shock index. By relying on the average shock index, the monitor-defibrillator 102 reduces the risk of generating an erroneous recommendation 118 due to transient artifact within the ECG 109. According to particular cases, the average shock index is based on shock indices calculated based on three to five (overlapping and/or nonoverlapping) segments of the ECG 109. In some examples, a shock index for a more recent segment of the ECG 109 is weighted more heavily than a shock index for a less recent segment of the ECG 109 in the average shock index. By weighting the shock indices based on recency of the corresponding segments, the recommendation 118 can be rapidly updated based on sudden changes in the cardiac rhythm of the patient 104.

According to various implementations, if the monitor-defibrillator 102 is unable to generate the recommendation 118 to reflect a shock or no-shock decision within a threshold time, the monitor-defibrillator 102 outputs a prompt to at least temporarily cease chest compressions (e.g., the monitor-defibrillator 102 outputs a "stop CPR" message). For instance, the monitor-defibrillator 102 continuously and/or repeatedly analyzes the shock indices of segments of the ECG 109, but the shock indices remain in an indeterminate range. The threshold time, for example, is in a range of 10 seconds to 2 minutes, such as 10 seconds, 30 seconds, or 1 minute. In various cases, the monitor-defibrillator 102 detects that chest compressions have ceased (e.g., based on a signal detected by the compression detector 112). Upon determining that the chest compressions have ceased, in some examples, the monitor-defibrillator 102 generates a shock index without removing chest compression artifacts from the ECG 109, because chest compression artifacts are absent from the ECG 109. The cessation of chest compressions, in some cases, increases the chance that the monitor-defibrillator 102 generates a recommendation 118 to reflect a shock or no-shock decision. Thus, by limiting the amount of time that the monitor-defibrillator 102 analyzes the ECG 109 with chest compression artifacts present, the rescuer 106 is able to rapidly respond to a shockable rhythm exhibited by the patient 104 even when the monitor-defibrillator 102 is unable to discern the shockable rhythm in view of the chest compression artifacts.

In some implementations, the monitor-defibrillator 102 performs multiple (sometimes overlapping) analyses of the ECG 109 (ora segment(s) thereof). In these implementations, if a shock index exceeds the shock advised threshold by more than a threshold amount (e.g., a "very shockable" result), the timing of ECG segments analyzed can be shortened in order to rapidly output a recommendation 118 to indicate that treating the patient 104 with a defibrillation shock is advised. In some examples, this implementation is asymmetric. That is, if a shock index is below the no shock advised threshold by more than a threshold amount, this may not lead to a rapid output of a recommendation 118 to indicate that treating the patient 104 with a defibrillation shock is not advised. This is because there is no particular hurry in a nonshockable situation. Rather, in a nonshockable situation, the rescuer 106 may perform additional CPR.

Figure 2:
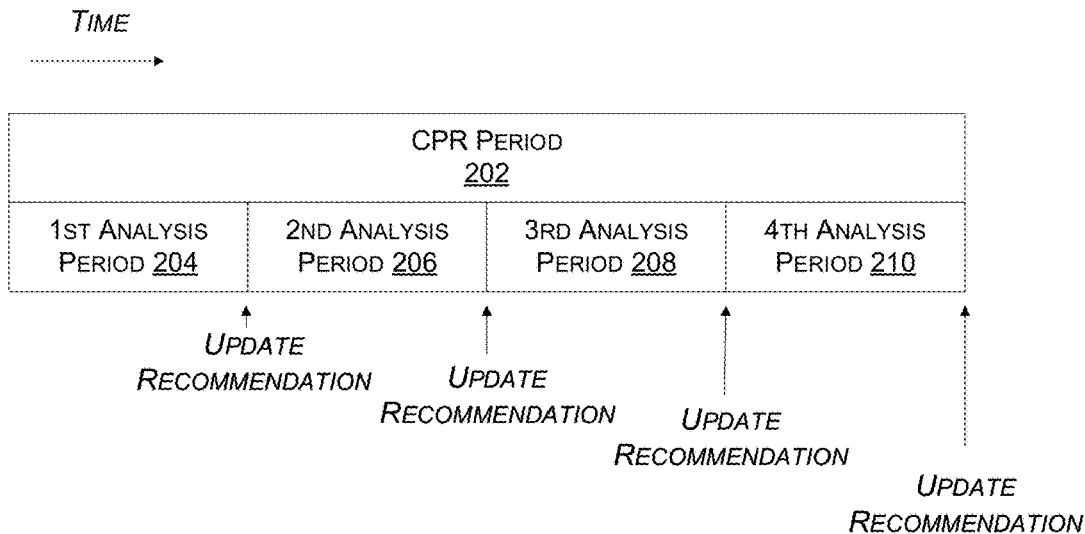
FIG. 2 illustrates an example timeline for repeatedly analyzing an ECG of an individual.

FIG. 2 illustrates an example timeline 200 for repeatedly analyzing an ECG of an individual. The timeline 200, for instance, reflects an analysis performed by a medical device, such as the monitor-defibrillator 102 described above with reference to FIG. 1. In FIG. 2, time increases from left to right, such that the left side of FIG. 2 depicts an earlier time than the right side of FIG. 2.

The timeline 200 includes a CPR period 202 that extends continuously from a start time to an end time. During the CPR period 202, the individual is receiving chest compressions (e.g., manually from a user or from a chest compression device) without pause. For instance, the chest compressions are administered at greater than a particular frequency (e.g., a frequency that is greater than or equal to 1 Hz and less than or equal to 3 Hz) during the CPR period 202. In some examples, the CPR period 202 has a predetermined duration (also referred to as a "length"). For example, the duration of the CPR period 202 is greater than or equal to 30 seconds and less than or equal to 3 minutes. In a particular case, the CPR period 202 is 2 minutes.

As the chest compressions are administered to the individual during the CPR period 202, the medical device detects and analyzes the ECG of the individual during a first analysis period 204, a second analysis period 206, a third analysis period 208, and a fourth analysis period 210. The medical device generates and/or outputs a recommendation during the CPR period 202. In some cases, the medical device refrains from outputting (e.g., hides) the recommendation until the medical device receives an input signal that activates an advisory mode.

During the first analysis period 204, the medical device detects a first segment of the ECG and determines whether the first segment includes a shockable rhythm (e.g., VF or pulseless V-Tach). The medical device generates a first shock decision based on the presence or absence of the shockable rhythm in the first segment. For example, the first shock decision is a shockable decision (indicating that the shockable rhythm is present), a nonshockable decision (indicating that the shockable rhythm is absent), or an indeterminate decision. The medical device updates the recommendation at the end of the first analysis period 204 based on the first shock decision.

In response to generating the first shock decision, the medical device detects a second segment of the ECG and determines whether the second segment includes the shockable rhythm during the second analysis period 206. The start time of the second analysis period 206 is simultaneous with or after the end time of the first analysis period 204. The medical device generates a second shock decision based on the presence or absence of the shockable rhythm in the second segment. The medical device updates the recommendation based on the presence or absence of the shockable rhythm in the second segment.

The third analysis period 208 and the fourth analysis period 210 proceed similarly to the first analysis period 204 and the second analysis period 206. During the third analysis period 208, the medical device detects a third segment of the ECG, determines whether the third segment includes the shockable rhythm, and generates a third shock decision based on the presence or absence of the shockable rhythm in the third segment. Similarly, during the fourth analysis period 210, the medical device detects a fourth segment of the ECG, determines whether the fourth segment includes the shockable rhythm, and generates a fourth shock decision based on the presence or absence of the shockable rhythm in the fourth segment. The medical device updates the recommendation based on the third shock decision and the fourth shock decision. The start time of the third analysis period 208 is simultaneous with or after the end time of the second analysis period 206. The start time of the fourth analysis period 210 is simultaneous with or after the end time of the third analysis period 208.

Although FIG. 2 illustrates that the first analysis period 204, the second analysis period 206, the third analysis period 208, and the fourth analysis period 210 have the same length, implementations of this disclosure are not so limited. For example, the first analysis period 204, the second analysis period 206, the third analysis period 208, and the fourth analysis period 210 can have different lengths. Furthermore, in some cases, the length of the CPR period 202 is less than or greater than the length of four analysis periods. For example, the medical device may perform less than or more than four analyses of four ECG segments during the course of the CPR period 202.

Figure 3:
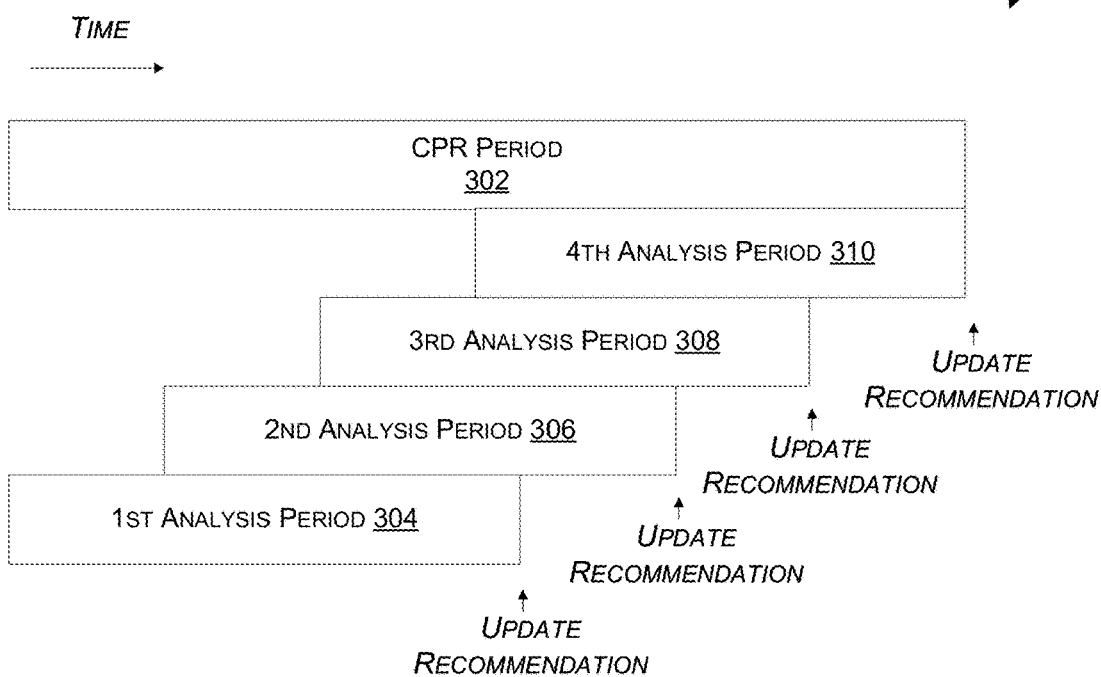
FIG. 3 illustrates an example timeline for periodically analyzing an ECG of an individual.

FIG. 3 illustrates an example timeline 300 for periodically analyzing an ECG of an individual. The timeline 300, for instance, reflects the analysis performed by the monitor-defibrillator 102 on the ECG 109 of the patient 104 described above with reference to FIG. 1. In FIG. 3, time increases from left to right, such that the left side of FIG. 3 depicts an earlier time than the right side of FIG. 3.

The timeline 300 includes a CPR period 302 that extends continuously from a start time to an end time. During the CPR period 302, the individual is receiving chest compressions (e.g., manually from a user or from a chest compression device) without pause. For instance, the chest compressions are administered at greater than a particular frequency (e.g., a frequency that is greater than or equal to 1 Hz and less than or equal to 3 Hz) during the CPR period 302. In some examples, the CPR period 302 has a predetermined duration (also referred to as a "length"). For example, the duration of the CPR period 302 is greater than or equal to 30 seconds and less than or equal to 3 minutes. In a particular case, the CPR period 302 is 2 minutes.

As the chest compressions are administered to the individual during the CPR period 302, the medical device detects and analyzes the ECG of the individual during a first analysis period 304, a second analysis period 306, a third analysis period 308, and a fourth analysis period 310. The medical device generates and/or outputs a recommendation during the CPR period 302. In some cases, the medical device refrains from outputting (e.g., hides) the recommendation until the medical device receives an input signal that activates an advisory mode.

During the first analysis period 304, the medical device detects a first segment of the ECG and determines whether the first segment includes a shockable rhythm (e.g., VF or pulseless V-Tach). The medical device generates a first shock decision based on the presence or absence of the shockable rhythm in the first segment. For example, the first shock decision is a shockable decision (indicating that the shockable rhythm is present), a nonshockable decision (indicating that the shockable rhythm is absent), or an indeterminate decision. The medical device updates the recommendation at the end of the first analysis period 304 based on the first shock decision.

During the second analysis period 306, the medical device detects a second segment of the ECG, determines whether the second segment includes the shockable rhythm, and updates the recommendation based on whether the second segment includes the shockable rhythm. The second analysis period 306 overlaps with the first analysis period 304. As shown in FIG. 3, the start time of the second analysis period 306 occurs prior to the end time of the first analysis period 304.

During the third analysis period 308, the medical device detects a third segment of the ECG, determines whether the second segment includes the shockable rhythm, and updates the recommendation based on whether the second segment includes the shockable rhythm. The third analysis period 308 overlaps with the second analysis period 306 and the first analysis period 304. As shown in FIG. 3, the start time of the third analysis period 308 occurs prior to the end time of the first analysis period 304 and the end time of the second analysis period 306.

During the fourth analysis period 310, the medical device detects a third segment of the ECG, determines whether the second segment includes the shockable rhythm, and updates the recommendation based on whether the second segment includes the shockable rhythm. The fourth analysis period 310 overlaps with the third analysis period 308, the second analysis period 306, and the first analysis period 304. As shown in FIG. 3, the start time of the fourth analysis period 310 occurs prior to the end time of the first analysis period 304, the end time of the second analysis period 306, and the end time of the third analysis period 308.

Note that by this process, the updating to the recommendations is more frequent than in FIG. 2 even though the analysis periods are longer.

In some cases, the start times of the first analysis period 304, the second analysis period 306, the third analysis period 308, and the fourth analysis period 310 are separated by a particular period. In some cases, the start times are separated by different periods. In the example of FIG. 3, the particular period is shorter than the respective durations of the first analysis period 304, the second analysis period 306, the third analysis period 308, and the fourth analysis period 310. Due to the overlapping analysis periods 304, 306, 308, and 310, the medical device detects and/or analyzes multiple segments of the ECG in parallel. Thus, in some examples, at a particular time point, the medical device is analyzing multiple segments of the ECG simultaneously.

According to some examples, the medical device adjusts the period(s) separating the start times and/or otherwise adjusts the number of segments being analyzed simultaneously based on a processing load on the medical device. For instance, the medical device executes computing tasks via n computing channels, wherein n is a positive integer. The medical device analyzes m segments of the ECG, in parallel, using m of the n computing channels, wherein m is a positive integer that is less than n. In some cases, the medical device limits m based on the number of available computing channels among the n computing channels. For example, the medical device is using o computing channels for non-ECG-analysis tasks, such as analysis of other physiological parameters (e.g., heart rate, temperature, blood pressure, etc.), graphical output tasks, and the like. In these cases, the medical device limits m to be no greater than n minus o. According to some examples, the medical device adjusts the period between start times of the analysis periods 304, 306, 308, and 310 based on the value of m. In some cases, the medical device waits to begin an analysis period until a time point at which less than m segments are being analyzed.

Although FIG. 3 illustrates that the first analysis period 304, the second analysis period 306, the third analysis period 308, and the fourth analysis period 310 have the same length, implementations of this disclosure are not so limited. For example, the first analysis period 304, the second analysis period 306, the third analysis period 308, and the fourth analysis period 310 can have different lengths. Furthermore, in some cases, the length of the CPR period 302 is less than or greater than the time between the start time of the first analysis period 304 and the end time of the fourth analysis period 310. For example, the medical device may perform less than or more than four analyses of four ECG segments during the course of the CPR period 302.

Figure 4:
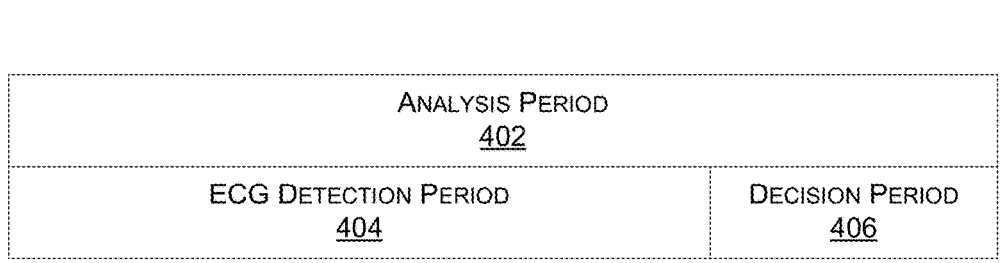
FIG. 4 illustrates an example timeline for analyzing a segment of an ECG.

FIG. 4 illustrates an example timeline 400 for analyzing a segment of an ECG. The example timeline 400 includes a single analysis period 402. In various examples, the analysis period 402 is the first analysis period 204, the second analysis period 206, the third analysis period 208, or the fourth analysis period 210 described above with reference to FIG. 2. In some cases, the analysis period 402 is the first analysis period 304, the second analysis period 306, the third analysis period 308, or the fourth analysis period 310 described above with reference to FIG. 3.

An ECG detection period 404 occurs during the analysis period 402. During the ECG detection period 404, a medical device detects a segment of an ECG of an individual. The individual is receiving chest compressions during the ECG detection period 404, for instance. Thus, the segment includes an artifact associated with the chest compressions.

Once the segment is detected, the medical device analyzes the segment during a decision period 406. The decision period 406 occurs during the analysis period 402. During the decision period 406, the medical device determines whether the segment of the ECG includes a shockable rhythm. For example, the medical device generates a filtered segment by (at least partially) removing the artifact associated with the chest compressions from the segment detected during the ECG detection period 404. In some cases, the medical device removes at least a portion of the artifact by applying a filter to the detected ECG segment, such as an adaptive filter (e.g., a Wiener filter, a Kalman filter, or the like), a comb filter, an inverse comb filter, a high-pass filter, a band reject filter, a finite impulse response (FIR) filter, an infinite impulse response (IIR) filter, or a combination thereof. In some cases, the medical device converts the ECG from the time domain into the frequency (e.g., a Fourier) domain, a Laplace domain, a Z-transform domain, or a wavelet (e.g., a continuous wavelet transform, a discrete wavelet transform, etc.) domain, and removes the chest compression artifact by analyzing the converted ECG. According to some examples, the medical device identifies and subtracts the chest compression artifact. For instance, the medical device detects chest compressions being applied to the individual during the ECG detection period 402 and identifies and/or subtracts the chest compression artifact based on the detected chest compressions.

In some examples, the medical device generates a shock index based on the filtered segment. The shock index, for instance, corresponds to a likelihood that the filtered segment includes the shockable rhythm. In some examples, the medical device generates the shock index by deriving, from the filtered segment, one or more parameters that are associated with the shockable rhythm. These parameters, for example, include features that are indicative of the shockable rhythm, such as a spectral signature of the shockable rhythm, a dominant frequency indicative of the shockable rhythm, or the like. The medical device fits the parameter(s) to a model (e.g., a logistic regression model, a machine learning model, or the like) that has been derived based on previously observed shockable rhythms.

In various implementations, the medical device determines whether the shockable rhythm is present by comparing the shock index to at least one threshold. The medical device generates a shock decision based on the comparison. For example, the medical device determines that the shockable rhythm is present if the shock index is greater than a first threshold and a second threshold (a shockable decision), determines that the shockable rhythm is absent if the shock index is less than the first threshold and the second threshold (a nonshockable decision), and is unable to determine whether the shockable rhythm is present or absent to a sufficient level of certainty if the shock index is greater than the first threshold and less than the second threshold (an indeterminate decision). In some cases, the medical device generates and/or updates a recommendation based on the shock decision. By the end time of the decision period 406, the medical device generates the shock decision, generates the recommendation based on the shock decision, and/or updates the recommendation based on the shock decision.

Although FIG. 4 illustrates a particular relative length of the ECG detection period 404 to the decision period 406, these lengths are not necessarily illustrated to scale. For example, in some cases, the decision period 406 is shorter relative to the ECG detection period 404 than indicated in FIG. 4.

Figure 5:
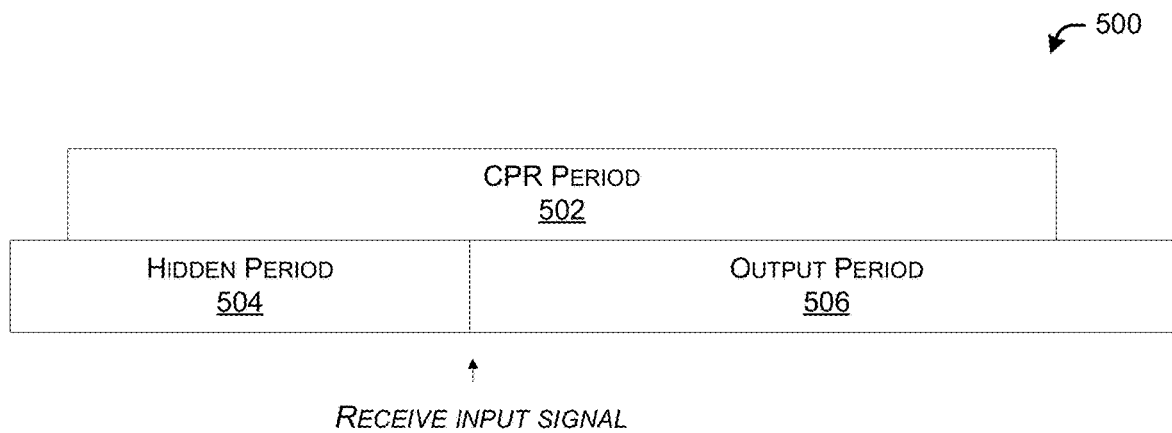
FIG. 5 illustrates an example timeline for outputting a recommendation on-demand during a CPR period.

FIG. 5 illustrates an example timeline 500 for outputting a recommendation on-demand during a CPR period 502. In some implementations, the CPR period 502 of FIG. 5 is the CPR period 202 of FIG. 2 or the CPR period 302 of FIG. 3. In various examples, the example timeline 500 is utilized by a medical device, such as the monitor-defibrillator 102 described above with reference to FIG. 1.

A hidden period 504 overlaps with the CPR period 502. During the hidden period 504, the medical device refrains from outputting a recommendation to a user. For instance, the recommendation is "hidden" from the user. In various examples, the medical device determines at least one shock decision, generates the recommendation, updates the recommendation, or a combination thereof, during the hidden period 504. By hiding the recommendation from the user, in some examples, the medical device provides a simplified user interface for the user.

When the medical device receives an input signal, the hidden period 504 ends and an output period 506 starts. The output period 506 overlaps with the CPR period 502. During the output period 506, the medical device outputs the recommendation. Because the recommendation has already been generated and/or a shock decision has already been made by the time the medical device receives the input signal, the medical device outputs the recommendation immediately during the output period 506 or without significant delay (e.g., less than 5 seconds, 4 seconds, 3 seconds, 2 seconds or 1 second). For instance, if there is a delay between the medical device receiving the input signal and outputting the recommendation, that delay has a shorter duration than an analysis period of the medical device. The output period 506 is simultaneous with an active period of an analysis mode of the medical device. For example, the input signal causes the medical device to activate the analysis mode described above with reference to FIG. 1. During the output period 506, the medical device continues to generate at least one shock decision and update the recommendation based on the shock decision(s).

In various examples, the hidden period 504 begins prior to the CPR period 502 and/or the output period 506 ends after the CPR period 502. Before or after the CPR period 502, the medical device makes at least one shock decision, generates the recommendation, and/or updates the recommendation based on an ECG from an individual who is not receiving chest compressions. Thus, the medical device makes at least one shock decision, generates the recommendation, and/or updates the recommendation without filtering the ECG. However, during the CPR period 502, the medical device makes at least one shock decision, generates the recommendation, and/or updates the recommendation based on at least one filtered ECG segment, wherein the medical device generates the filtered ECG segment(s) by at least partially removing a chest compression artifact from unfiltered ECG segment(s).

Figure 6:
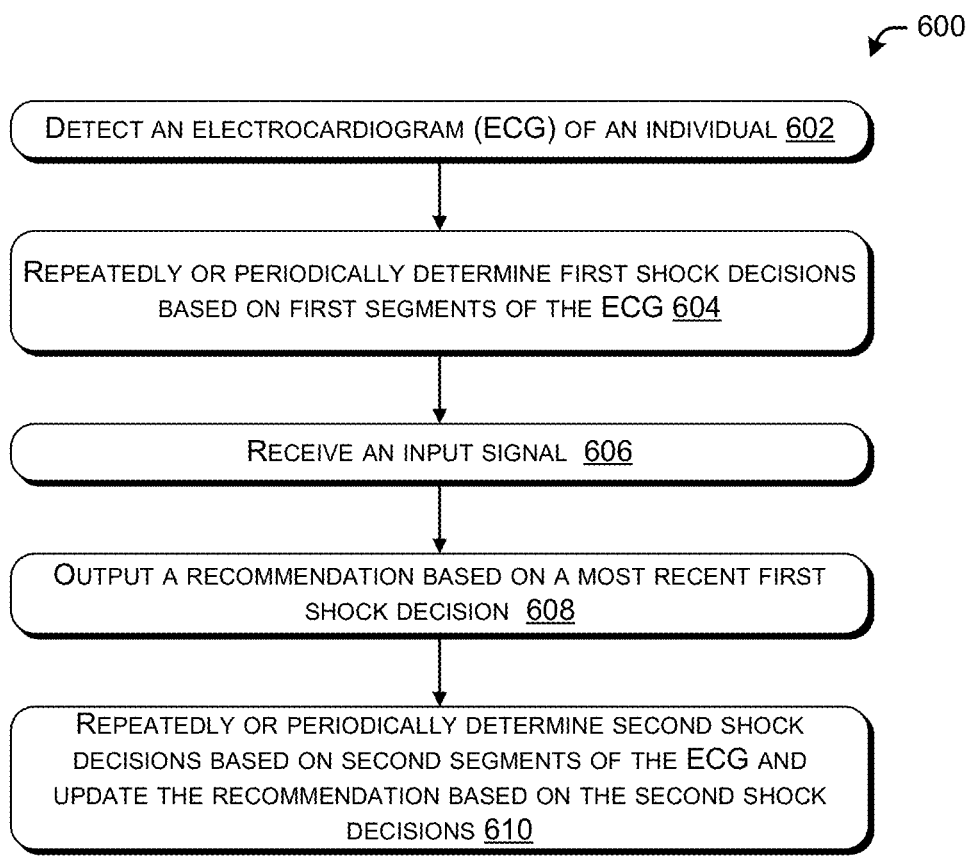
FIG. 6 illustrates an example process for providing an on-demand recommendation indicating whether to administer a defibrillation shock to an individual.
Figure 7:
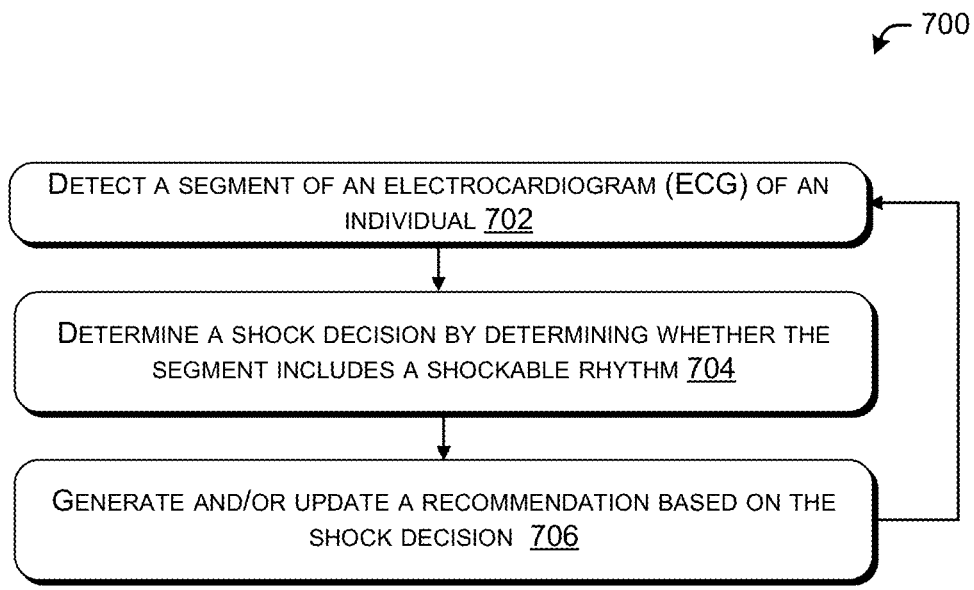
FIG. 7 illustrates an example process for repeatedly analyzing segments of an ECG of an individual in order to provide a recommendation about whether to administer a defibrillation shock to the individual.
Figure 8:
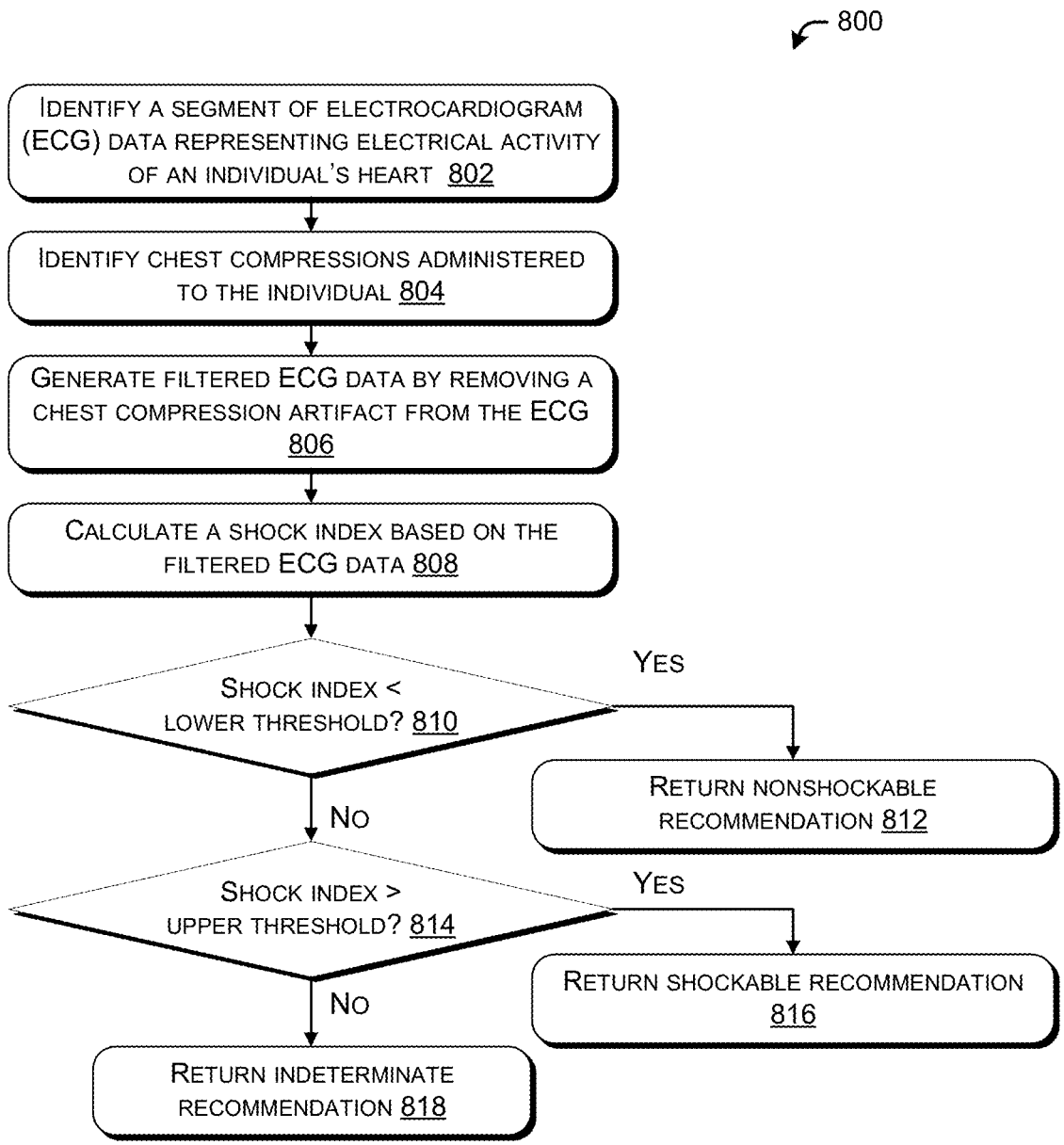
FIG. 8 illustrates an example process for determining whether a shockable rhythm is present in ECG data that includes a chest compression artifact.

FIGS. 6 to 8 illustrate processes in accordance with various implementations of the present disclosure. Although the processes in FIGS. 6 to 8 are illustrated in particular orders, implementations of the present disclosure are not necessarily limited to the particular orders depicted in FIGS. 6 to 8.

FIG. 6 illustrates an example process 600 for providing an on-demand recommendation indicating whether to administer a defibrillation shock to an individual. The process 600 is performed by a medical device, such as the monitor-defibrillator 102 described above with reference to FIG. 1 and/or any medical device described above with reference to FIGS. 2-5.

At 602, the medical device detects an ECG of an individual. In various examples, the individual is receiving chest compressions, such that the ECG includes a chest compression artifact. The medical device detects the ECG, for instance, by a detection circuit.

At 604, the medical device repeatedly or periodically determines first shock decisions based on first segments of the ECG. In some examples, the medical device repeatedly determines the first shock decisions by reevaluating a new segment of the ECG each time the medical device arrives at a shock decision. In some implementations, the medical device periodically evaluates segments of the ECG as they are detected. In some examples, a period at which the medical device evaluates the segments is shorter than a duration of an analysis period of an individual segment, such that the medical device performs multiple parallel analyses of the ECG at a given time.

The medical device determines each shock decision by filtering the chest compression artifact from the appropriate segment. For instance, the medical device applies a filter to the detected ECG segment, such as an adaptive filter (e.g., a Wiener filter, a Kalman filter, or the like), a comb filter, an inverse comb filter, a high-pass filter, a band reject filter, an FIR filter, an IIR filter, or a combination thereof. In some cases, the medical device converts the ECG from the time domain into the frequency (e.g., a Fourier) domain, a Laplace domain, a Z-transform domain, or a wavelet (e.g., a continuous wavelet transform, a discrete wavelet transform, etc.) domain, and removes the chest compression artifact by analyzing the converted ECG. In some examples, the medical device transforms or maps the ECG segment to a different domain in which the chest compression artifact is insignificant. According to some examples, the medical device identifies and subtracts the chest compression artifact. For instance, the medical device detects chest compressions being applied to the individual during the ECG detection period 402 and identifies and/or subtracts the chest compression artifact based on the detected chest compressions.

The medical device generates a shock index based on the filtered segment. The shock index, for example, corresponds to a probability and/or certainty that the filtered segment includes a shockable rhythm (e.g., VF or pulseless V-Tach). In various examples, the medical device generates the shock decision by comparing the shock index to one or more thresholds. For example, if the shock index is greater than a first threshold and a second threshold, the shock decision for the segment is a shockable decision; if the shock index is less than the first threshold and the second threshold, the shock decision for the segment is a nonshockable decision; and if the shock index is between the first threshold and the second threshold, the shock decision for the segment is indeterminate. In some examples, the medical device generates a shock decision for each of the first segments as they are detected by the medical device.

At 606, the medical device receives an input signal. The medical device receives the input signal, for instance, at an input device. The medical device receives the input signal from a user, in various examples.

At 608, the medical device outputs a recommendation based on a most recent first shock decision. In various examples, the input signal causes the medical device to activate an analysis mode. The recommendation is output from an output device (e.g., a screen) of the medical device. The recommendation indicates whether administration of a defibrillation shock to the individual is advised. The medical device generates the recommendation based on a shock decision corresponding to a most recent, evaluated segment of the ECG. In this example, the most recent segment of the ECG is the latest first segment evaluated at 606. Thus, the shock decision was determined prior to the medical device receiving the input signal at 606, for instance. For example, the medical device generates the recommendation to indicate that a defibrillation shock is advised if the most recent shock decision was a shockable decision, to indicate that a defibrillation shock is not advised if the most recent shock decision was a nonshockable decision, and to indicate that further analysis is needed and/or a pause in chest compressions is advised if the most recent shock decision was indeterminate. As a result, the medical device outputs the recommendation faster than the medical device would take to evaluate a new segment of the ECG.

At 610, the medical device repeatedly or periodically determines second shock decisions based on second segments of the ECG and updates the recommendation based on the second shock decisions. The medical device detects at least some of the second segments after receiving the input signal. The medical device continues to analyze the second segments of the ECG after receiving the input signal. The second segments are analyzed similarly to the first segments, for instance. Upon determining each shock decision of the second segments, the medical device updates the recommendation accordingly. In some cases, the medical device determines certainties of the shock decisions and updates the recommendation based on the certainties. For instance, the medical device outputs the recommendation with an average (e.g., a running average) of the certainties. Thus, the medical device provides an up-to-date recommendation for the user.

FIG. 7 illustrates an example process 700 for repeatedly analyzing segments of an ECG of an individual in order to provide a recommendation about whether to administer a defibrillation shock to the individual. The process 700 is performed by a medical device, such as the monitor-defibrillator 102 described above with reference to FIG. 1 and/or any medical device described above with reference to FIGS. 2-5.

At 702, the medical device detects a segment of an ECG of an individual. In various examples, the individual is receiving chest compressions, such that the segment includes a chest compression artifact. The medical device detects the segment, for instance, by a detection circuit.

At 704, the medical device determines a shock decision by determining whether the segment includes a shockable rhythm. The medical device determines the shock decision by filtering the chest compression artifact from the segment. For instance, the medical device applies a filter to the detected ECG segment, such as an adaptive filter (e.g., a Wiener filter, a Kalman filter, or the like), a comb filter, an inverse comb filter, a high-pass filter, a band reject filter, a finite impulse response (FIR) filter, an infinite impulse response (IIR) filter, or a combination thereof. In some cases, the medical device converts the ECG from the time domain into the frequency (e.g., a Fourier) domain, a Laplace domain, a Z-transform domain, or a wavelet (e.g., a continuous wavelet transform, a discrete wavelet transform, etc.) domain, and removes the chest compression artifact by analyzing the converted ECG. According to some examples, the medical device identifies and subtracts the chest compression artifact. For instance, the medical device detects chest compressions being applied to the individual during the ECG detection period 402 and identifies and/or subtracts the chest compression artifact based on the detected chest compressions. The medical device generates a shock index based on the filtered segment. The shock index, for example, corresponds to a probability and/or certainty that the filtered segment includes a shockable rhythm (e.g., VF or pulseless V-Tach). In various examples, the medical device generates the shock decision by comparing the shock index to one or more thresholds. For example, if the shock index is greater than a first threshold and a second threshold, the shock decision for the segment is a shockable decision; if the shock index is less than the first threshold and the second threshold, the shock decision for the segment is a nonshockable decision; and if the shock index is between the first threshold and the second threshold, the shock decision for the segment is indeterminate. In some examples, the medical device further determines a certainty of the shock decision. For example, the medical device determines the certainty based on the shock index.

At 706, the medical device generates and/or updates a recommendation based on the shock decision. In some examples, when the medical device is not in an analysis mode, the medical device generates the recommendation without outputting the recommendation. Thus, a user interface of the medical device is simplified when the medical device is not in the analysis mode. However, when the medical device is in analysis mode, the medical device outputs the recommendation. The recommendation is based on the shock decision generated at 704. For example, the medical device generates the recommendation to indicate that a defibrillation shock is advised if the shock decision was a shockable decision, to indicate that a defibrillation shock is not advised if the shock decision was a nonshockable decision, and to indicate that further analysis is needed and/or a pause in chest compressions is advised if the shock decision was indeterminate. In various examples, the medical device updates a recommendation that has already been output based on the shock decision. In some instances, the medical device generates and/or updates the recommendation to include the certainty of the shock decision.

As shown in FIG. 7, the process 700 is repeated. In some examples, the process 700 is repeated during a CPR period during which chest compressions are administered to the individual at greater than a threshold frequency. The CPR period omits pauses to the chest compressions, for instance.

FIG. 8 illustrates an example process 800 for identifying a shockable rhythm in ECG data that includes a chest compression artifact. The process 800 is performed by a medical device, such as the monitor-defibrillator 102 described above with reference to FIG. 1 and/or any medical device described above with reference to FIGS. 2-5.

At 802, the medical device identifies a segment of ECG data representing an electrical activity of an individual's heart when the individual is receiving chest compressions. The ECG data is obtained by detecting one or more relative voltages between electrodes connected to the chest of the individual, for instance. The ECG data is digital data representing the detected voltages, for example. According to various implementations, the chest compressions generate noise in the ECG data. The noise is at least partly based on jostling or movement of the electrodes on the skin of the individual, for example. An artifact is present in the ECG data based on the chest compressions. If the raw ECG data is output to a user, the chest compression artifact makes the ECG data difficult for the user to evaluate, in some cases. For instance, the user may have difficulty manually discerning whether a shockable rhythm (e.g., VF or pulseless V-Tach) is present in the ECG data. Accordingly, the medical device removes the artifact and automatically determines whether the shockable rhythm is present.

The segment is selected from the ECG data. As used herein, the term "segment" can refer to a subset of data that are obtained from a first time to a second time, wherein the first time occurs after the time of the first datapoint in the data and/or the second time occurs before the time of the last datapoint in the data. In some cases, the data in the segment are obtained over a time interval. The time interval, for example, is at least a minimum period and no longer than a maximum period. The minimum period, for instance, is 3 seconds, 4 seconds, 7 seconds, 10 seconds, or another time interval. The maximum period, for example, is 12 seconds, 20 seconds, or some other time interval. In some cases, the medical device determines the time interval, the minimum period, the maximum period, or a combination thereof, based on whether the individual has been previously shocked by the medical device (e.g., within a particular time interval, such as the previous 10 minutes). For example, the maximum period is relatively long (e.g., 12 seconds) if the individual has been previously shocked, and is relatively short (e.g., 8 seconds) if the individual has not been previously shocked.

At 804, the medical device identifies a timing of chest compressions administered to the individual. In some cases, the medical device determines when the chest compressions are administered based on a signal from a chest compression monitor, which in some cases is disposed on the chest of the individual includes at least one accelerometer and/or gyroscope that detects chest compressions administered to the individual. In some examples, the medical device detects an electrical impedance between two or more electrodes in contact with the individual and determines when the chest compressions are administered based on the electrical impedance. In some examples, the medical device detects the chest compressions using image processing of images depicting the individual, the chest compression monitor, a devise administering the chest compressions, and/or a rescuer administering the chest compressions; triangulation of RFID tags within the chest compression monitor and/or attached to the individual; or the like.

At 806, the medical device removes the chest compression artifact of the selected segment of the ECG data. The chest compression artifact has a fundamental that is between 1.5 to 2 Hz, in various examples. However, heart rhythm features (e.g., a VF rhythm, a V-tach rhythm, QRS complexes, and other inherent heart rhythms) are typically defined by higher frequencies. In some examples, the medical device applies a filter to the detected ECG segment, such as an adaptive filter (e.g., a Wiener filter, a Kalman filter, or the like), a comb filter, an inverse comb filter, a high-pass filter, a band reject filter, a finite impulse response (FIR) filter, an infinite impulse response (IIR) filter, or a combination thereof. In some cases, the medical device converts the ECG from the time domain into the frequency (e.g., a Fourier) domain, a Laplace domain, a Z-transform domain, or a wavelet (e.g., a continuous wavelet transform, a discrete wavelet transform, etc.) domain, and removes the chest compression artifact by analyzing the converted ECG. According to some examples, the medical device identifies and subtracts the chest compression artifact. For instance, the medical device detects chest compressions being applied to the individual during the ECG detection period 402 and identifies and/or subtracts the chest compression artifact based on the detected chest compressions.

Optionally, the medical device applies additional filtering techniques to reduce the harmonics of the chest compression artifact in the selected segment of the ECG data. For example, the medical device applies a comb filter with multiple stopbands that correspond to the fundamental frequency of the chest compressions administered to the individual and one or more harmonics of the fundamental frequency.

At 808, the medical device calculates a shock index based on the filtered segment. According to some implementations, the medical device generates a shockable rhythm score and generates the shock index based on the shockable rhythm score. The shockable rhythm score corresponds to a similarity between the filtered segment and a shockable rhythm. In some cases, the shockable rhythm score is a continuous variable that ranges between a lower bound (e.g., 0) and an upper bound (e.g., 1).

At 810, the medical device determines whether the shock index is less than a lower threshold. The lower threshold is selected, for instance, based on an acceptable level of uncertainty regarding a nonshockable recommendation. In some cases, the lower threshold is user-selected, such that the lower threshold is calculated based on an input signal from a user. If the medical device determines that the shock index is less than the lower threshold, the medical device returns a nonshockable recommendation at 812.

If, on the other hand, the medical device determines that the shock index is greater than or equal to the lower threshold, the process 800 proceeds to 814. At 814, the medical device determines whether the shock index is greater than the upper threshold. The upper threshold is selected, for instance, based on an acceptable level of uncertainty regarding a shockable recommendation. In some cases, the upper threshold is user-selected, such that the upper threshold is calculated based on an input signal from a user. If the medical device determines that the shock index is greater than the upper threshold, the medical device returns a shockable recommendation at 816.

However, if the medical device determines that the shock index is less than or equal to the upper threshold, then the medical device returns an indeterminate recommendation at 818. The indeterminate decision means that the medical device is unable to conclude whether the shockable rhythm is present with a sufficient level of certainty. The level of certainty, in some cases, is predetermined and/or selected by a user.

In some cases, the medical device outputs (e.g., to a user) the recommendation, whether the shock recommendation is a nonshockable recommendation, a shockable recommendation, or an indeterminate recommendation. In some examples in which the medical device returns the indeterminate recommendation, the medical device outputs a recommendation to pause chest compressions in order to evaluate the ECG without the compression artifact present. The medical device and/or the user may be able to determine whether the shockable rhythm is present in the ECG without the compression artifact present, even if the medical device returned the indeterminate shock recommendation based on the ECG obtained while the chest compressions were administered to the individual.

Figure 9:
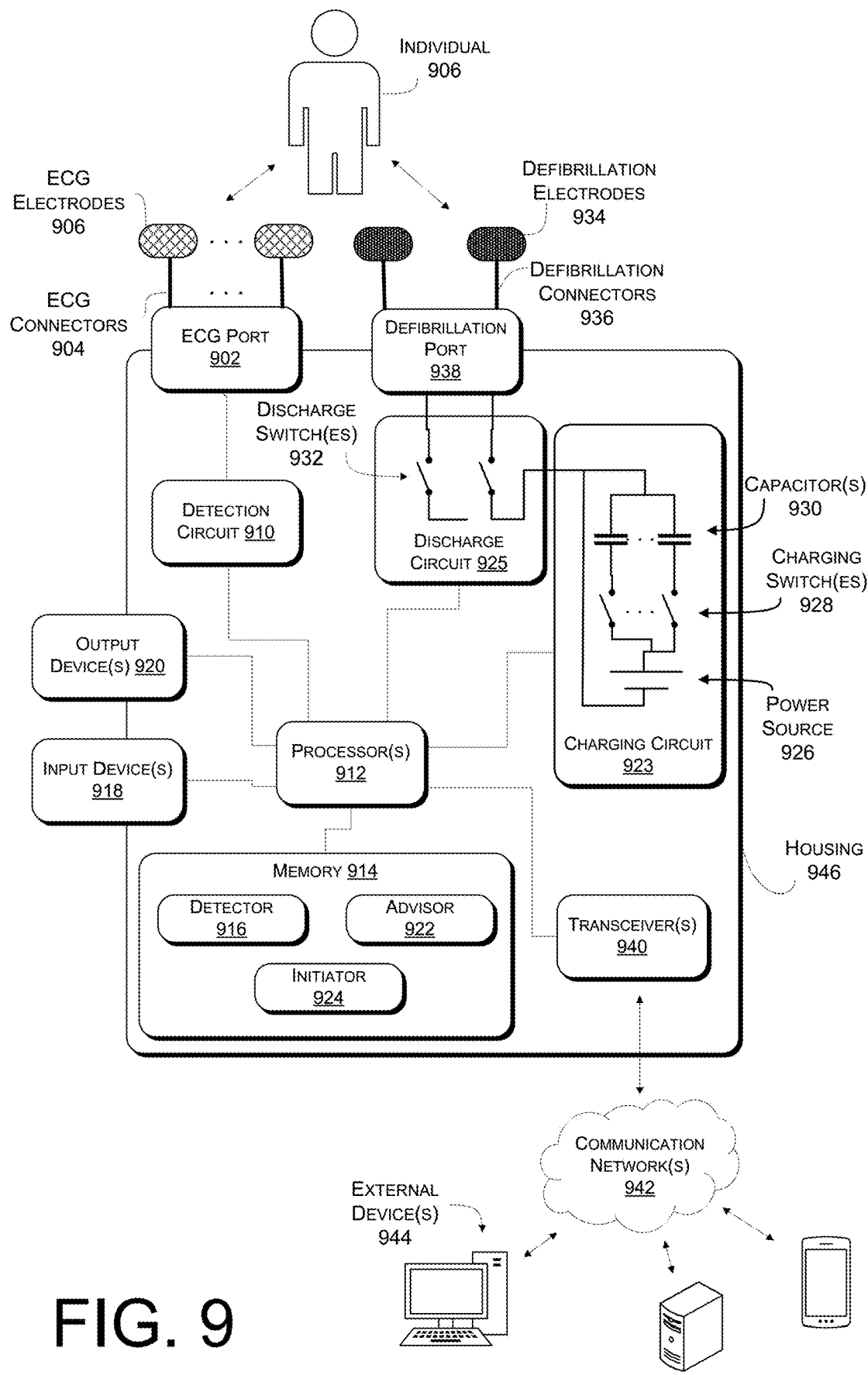
FIG. 9 illustrates an example of an external defibrillator configured to perform various functions described herein.

In various cases, the medical device performs the process 800 repeatedly, periodically, or a combination thereof. For example, upon returning a recommendation, the medical device repeats the process 800 by identifying another segment of ECG data. In some cases, the medical device initiates the process 800 (e.g., begins 802) at a particular frequency, such that the medical device may be performing the process 800 multiple times, in parallel, at a time. If the medical device determines multiple recommendations based on repeatedly and/or periodically performing the process 800, the medical device outputs (e.g., to the user) the most recently returned FIG. 9 illustrates an example of an external defibrillator 900 configured to perform various functions described herein. For example, the external defibrillator 900 is the monitor-defibrillator 102 described above with reference to FIG. 1 and/or any medical device described above with reference to FIGS. 2-5.

The external defibrillator 900 includes an electrocardiogram (ECG) port 902 connected to multiple ECG connectors 904. In some cases, the ECG connectors 904 are removeable from the ECG port 902. For instance, the ECG connectors 904 are plugged into the ECG port 902. The ECG connectors 904 are connected to ECG electrodes 906, respectively. In various implementations, the ECG electrodes 906 are disposed on different locations on an individual 908. A detection circuit 910 is configured to detect relative voltages between the ECG electrodes 906. These voltages are indicative of the electrical activity of the heart of the individual 908.

In various implementations, the ECG electrodes 906 are in contact with the different locations on the skin of the individual 908. In some examples, a first one of the ECG electrodes 906 is placed on the skin between the heart and right arm of the individual 908, a second one of the ECG electrodes 906 is placed on the skin between the heart and left arm of the individual 908, and a third one of the ECG electrodes 906 is placed on the skin between the heart and a leg (either the left leg or the right leg) of the individual 908. In these examples, the detection circuit 908 is configured to measure the relative voltages between the first, second, and third ECG electrodes 906. Respective pairings of the ECG electrodes 906 are referred to as "leads," and the voltages between the pairs of ECG electrodes 906 are known as "lead voltages." In some examples, more than three ECG electrodes 906 are included, such that 5-lead or 12-lead ECG signals are detected by the detection circuit 910.

The detection circuit 910 includes at least one analog circuit, at least one digital circuit, or a combination thereof. The detection circuit 910 receives the analog electrical signals from the ECG electrodes 906, via the ECG port 902 and the ECG connectors 904. In some cases, the detection circuit 910 includes one or more analog filters configured to filter noise and/or artifact from the electrical signals. The detection circuit 910 includes an analog-to-digital (ADC) in various examples. The detection circuit 910 generates a digital signal indicative of the analog electrical signals from the ECG electrodes 906. This digital signal can be referred to as an "ECG signal" or an "ECG."

In some cases, the detection circuit 910 further detects an electrical impedance between at least one pair of the ECG electrodes 906. For example, the detection circuit 910 includes, or otherwise controls, a power source that applies a known voltage across a pair of the ECG electrodes 906 and detects a resultant current between the pair of the ECG electrodes 906. The impedance is generated based on the applied voltage and the resultant current. In various cases, the impedance corresponds to respiration of the individual 908, chest compressions performed on the individual 908, and other physiological states of the individual 908. In various examples, the detection circuit 910 includes one or more analog filters configured to filter noise and/or artifact from the resultant current. The detection circuit 910 generates a digital signal indicative of the impedance using an ADC. This digital signal can be referred to as an "impedance signal" or an "impedance."

The detection circuit 910 provides the ECG signal and/or the impedance signal one or more processors 912 in the external defibrillator 900. In some implementations, the processor(s) 912 includes a central processing unit (CPU), a graphics processing unit (GPU), both CPU and GPU, or other processing unit or component known in the art.

The processor(s) 912 is operably connected to memory 914. In various implementations, the memory 912 is volatile (such as random access memory (RAM)), non-volatile (such as read only memory (ROM), flash memory, etc.) or some combination of the two. The memory 914 stores instructions that, when executed by the processor(s) 912, causes the processor(s) 912 to perform various operations. In various examples, the memory 914 stores methods, threads, processes, applications, objects, modules, any other sort of executable instruction, or a combination thereof. In some cases, the memory 914 stores files, databases, or a combination thereof. In some examples, the memory 914 includes, but is not limited to, RAM, ROM, electrically erasable programmable read-only memory (EEPROM), flash memory, or any other memory technology. In some examples, the memory 914 includes one or more of CD-ROMs, digital versatile discs (DVDs), content-addressable memory (CAM), or other optical storage, magnetic cassettes, magnetic tape, magnetic disk storage or other magnetic storage devices, or any other medium which can be used to store the desired information and which can be accessed by the processor(s) 912 and/or the external defibrillator 900. In some cases, the memory 914 at least temporarily stores the ECG signal and/or the impedance signal.

In various examples, the memory 914 includes a detector 916, which causes the processor(s) 912 to determine, based on the ECG signal and/or the impedance signal, whether the individual 908 is exhibiting a particular heart rhythm. For instance, the processor(s) 912 determines whether the individual 908 is experiencing a shockable rhythm that is treatable by defibrillation. Examples of shockable rhythms include ventricular fibrillation (VF) and pulseless ventricular tachycardia (V-Tach). In some examples, the processor(s) 912 determines whether any of a variety of different rhythms (e.g., asystole, sinus rhythm, atrial fibrillation (AF), etc.) are present in the ECG signal. According to various examples, the processor(s) 912 operating the detector 916 repeatedly and/or periodically evaluates segments of the ECG signal and determines shock decisions based on the segments of the ECG signals. In some cases, the processor(s) 912 evaluate multiple segments, simultaneously, at a given time.

The processor(s) 912 is operably connected to one or more input devices 918 and one or more output devices 920. Collectively, the input device(s) 918 and the output device(s) 920 function as an interface between a user and the defibrillator 900. The input device(s) 918 is configured to receive an input from a user and includes at least one of a keypad, a cursor control, a touch-sensitive display, a voice input device (e.g., a speaker), a haptic feedback device, or any combination thereof. The output device(s) 920 includes at least one of a display, a speaker, a haptic output device, a printer, or any combination thereof. In various examples, the processor(s) 912 causes a display among the input device(s) 918 to visually output a waveform of the ECG signal and/or the impedance signal. In some implementations, the input device(s) 918 includes one or more touch sensors, the output device(s) 920 includes a display screen, and the touch sensor(s) are integrated with the display screen. Thus, in some cases, the external defibrillator 900 includes a touchscreen configured to receive user input signal(s) and visually output physiological parameters, such as the ECG signal and/or the impedance signal.

In some examples, the memory 914 includes an advisor 922, which, when executed by the processor(s) 912, causes the processor(s) 912 to generate a recommendation (e.g., of whether to administer a defibrillation shock) and/or control the output device(s) 920 to output the advice to a user (e.g., a rescuer). In some examples, the processor(s) 912 provides, or causes the output device(s) 920 to provide, an instruction to perform CPR on the individual 908. In some cases, the processor(s) 912 evaluates, based on the ECG signal, the impedance signal, or other physiological parameters, CPR being performed on the individual 908 and causes the output device(s) 920 to provide feedback about the CPR in the instruction. According to some examples, the processor(s) 912, upon identifying that a shockable rhythm is present in the ECG signal (e.g., a segment of the ECG signal), causes the output device(s) 920 to output an instruction and/or recommendation to administer a defibrillation shock to the individual 908. In some cases, the processor(s) 912 selectively outputs the recommendation when an analysis mode has been activated. The processor(s) 912, for instance, updates the recommendation upon generating each shock decision of the segments of the ECG signal.

The memory 914 also includes an initiator 924 which, when executed by the processor(s) 912, causes the processor(s) 912 to control other elements of the external defibrillator 900 in order to administer a defibrillation shock to the individual 908. In some examples, the processor(s) 912 executing the initiator 924 selectively causes the administration of the defibrillation shock based on determining that the individual 908 is exhibiting the shockable rhythm and/or based on an input from a user (received, e.g., by the input device(s) 918. In some cases, the processor(s) 912 causes the defibrillation shock to be output at a particular time, which is determined by the processor(s) 912 based on the ECG signal and/or the impedance signal.

The processor(s) 912 is operably connected to a charging circuit 922 and a discharge circuit 924. In various implementations, the charging circuit 922 includes a power source 926, one or more charging switches 928, and one or more capacitors 930. The power source 926 includes, for instance, a battery. The processor(s) 912 initiates a defibrillation shock by causing the power source 926 to charge at least one capacitor among the capacitor(s) 930. For example, the processor(s) 912 activates at least one of the charging switch(es) 928 in the charging circuit 922 to complete a first circuit connecting the power source 926 and the capacitor to be charged. Then, the processor(s) 912 causes the discharge circuit 924 to discharge energy stored in the charged capacitor across a pair of defibrillation electrodes 930, which are in contact with the individual 908. For example, the processor(s) 912 deactivates the charging switch(es) 928 completing the first circuit between the capacitor(s) 930 and the power source 926, and activates one or more discharge switches 932 completing a second circuit connecting the charged capacitor 930 and at least a portion of the individual 908 disposed between defibrillation electrodes 934.

The energy is discharged from the defibrillation electrodes 934 in the form of a defibrillation shock. For example, the defibrillation electrodes 934 are connected to the skin of the individual 908 and located at positions on different sides of the heart of the individual 908, such that the defibrillation shock is applied across the heart of the individual 908. The defibrillation shock, in various examples, depolarizes a significant number of heart cells in a short amount of time. The defibrillation shock, for example, interrupts the propagation of the shockable rhythm (e.g., VF or pulseless V-Tach) through the heart. In some examples, the defibrillation shock is 200 J or greater with a duration of about 0.015 seconds. In some cases, the defibrillation shock has a multiphasic (e.g., biphasic) waveform. The discharge switch (es) 932 are controlled by the processor(s) 912, for example. In various implementations, the defibrillation electrodes 934 are connected to defibrillation connectors 936. The defibrillation connectors 936 are connected to a defibrillation port 938, in implementations. According to various examples, the defibrillation connectors 936 are removable from the defibrillation port 938. For example, the defibrillation connectors 936 are plugged into the defibrillation port 938.

In various implementations, the processor(s) 912 is operably connected to one or more transceivers 940 that transmit and/or receive data over one or more communication networks 942. For example, the transceiver(s) 940 includes a network interface card (NIC), a network adapter, a local area network (LAN) adapter, or a physical, virtual, or logical address to connect to the various external devices and/or systems. In various examples, the transceiver(s) 940 includes any sort of wireless transceivers capable of engaging in wireless communication (e.g., radio frequency (RF) communication). For example, the communication network(s) 942 includes one or more wireless networks that include a $3^{rd}$ Generation Partnership Project (3GPP) network, such as a Long Term Evolution (LTE) radio access network (RAN) (e.g., over one or more LE bands), a New Radio (NR) RAN (e.g., over one or more NR bands), or a combination thereof. In some cases, the transceiver(s) 940 includes other wireless modems, such as a modem for engaging in WI-FI®, WIGIG®, WIMAX®, BLUETOOTH®, or infrared communication over the communication network(s) 942.

The defibrillator 900 is configured to transmit and/or receive data (e.g., ECG data, impedance data, data indicative of one or more detected heart rhythms of the individual 908, data indicative of one or more defibrillation shocks administered to the individual 908, etc.) with one or more external devices 944 via the communication network(s) 942. The external devices 944 include, for instance, mobile devices (e.g., mobile phones, smart watches, etc.), Internet of Things (IoT) devices, medical devices, computers (e.g., laptop devices, servers, etc.), or any other type of computing device configured to communicate over the communication network(s) 942. In some examples, the external device(s) 944 is located remotely from the defibrillator 900, such as at a remote clinical environment (e.g., a hospital). According to various implementations, the processor(s) 912 causes the transceiver(s) 940 to transmit data to the external device(s) 944. In some cases, the transceiver(s) 940 receives data from the external device(s) 944 and the transceiver(s) 940 provide the received data to the processor(s) 912 for further analysis.

In various implementations, the external defibrillator 900 also includes a housing 946 that at least partially encloses other elements of the external defibrillator 900. For example, the housing 946 encloses the detection circuit 910, the processor(s) 912, the memory 914, the charging circuit 922, the transceiver(s) 940, or any combination thereof. In some cases, the input device(s) 918 and output device(s) 920 extend from an interior space at least partially surrounded by the housing 946 through a wall of the housing 946. In various examples, the housing 946 acts as a barrier to moisture, electrical interference, and/or dust, thereby protecting various components in the external defibrillator 900 from damage.

In some implementations, the external defibrillator 900 is an automated external defibrillator (AED) operated by an untrained user (e.g., a bystander, layperson, etc.) and can be operated in an automatic mode. In automatic mode, the processor(s) 912 automatically identifies a rhythm in the ECG signal, makes a decision whether to administer a defibrillation shock, charges the capacitor(s) 930, discharges the capacitor(s) 930, or any combination thereof. In some cases, the processor(s) 912 controls the output device(s) 920 to output (e.g., display) a simplified user interface to the untrained user. For example, the processor(s) 912 refrains from causing the output device(s) 920 to display a waveform of the ECG signal and/or the impedance signal to the untrained user, in order to simplify operation of the external defibrillator 900.

In some examples, the external defibrillator 900 is a monitor-defibrillator utilized by a trained user (e.g., a clinician, an emergency responder, etc.) and can be operated in a manual mode or the automatic mode. When the external defibrillator 900 operates in manual mode, the processor(s)

912 cause the output device(s) 920 to display a variety of information that may be relevant to the trained user, such as waveforms indicating the ECG data and/or impedance data, notifications about detected heart rhythms, and the like.

EXAMPLE CLAUSES

1. A monitor-defibrillator, including: a detection circuit configured to detect an electrocardiogram (ECG) of an individual receiving chest compressions; an input device configured to receive an input signal from a user; a display configured to visually output a recommendation; a processor; and memory storing instructions that, when executed by the processor, cause the processor to perform operations including: identifying multiple segments of the ECG that respectively correspond to multiple time windows; generating multiple shock decisions by determining whether the multiple segments respectively include a shockable rhythm, each shock decision corresponding to one of the multiple segments, the input device receiving the input signal after the multiple shock decisions are generated; in response to the input device receiving the input signal, selecting a shock decision among the multiple shock decisions associated with a segment among the multiple segments that corresponds to a latest time window among the multiple time windows; generating the recommendation based on the selected shock decision and independent of other shock decisions among the multiple shock decisions; and causing the display to visually output the recommendation.
2. The monitor-defibrillator of clause 1, wherein generating the multiple shock decisions by determining whether the multiple segments include the shockable rhythm includes: repeatedly or periodically analyzing the ECG.
3. The monitor-defibrillator of clause 1 or 2, wherein the selected shock decision is generated during an analysis period, and wherein the analysis period is longer than a latency period defined between a time that the input device receives the input signal and a time that the display visually outputs the recommendation.
4. A medical device, including: a detection circuit configured to detect an electrocardiogram (ECG) of an individual; an input device configured to receive an input signal from a user; an output device configured to output a recommendation; a processor; and memory storing instructions that, when executed by the processor, cause the processor to perform operations including: generating a first shock decision by analyzing a first segment of the ECG that corresponds to a first time window; generating a second shock decision by analyzing a second segment of the ECG that corresponds to a second time window, a start time of the second time window occurring after a start time of the first time window; in response to the input device receiving the input signal, generating the recommendation based on the second shock decision; and causing the output device to output the recommendation.
5. The medical device of clause 4, wherein the individual is receiving chest compressions during the first time window and the second time window, wherein generating the first shock decision by analyzing the first segment of the ECG that corresponds to the first time window includes: generating a first filtered segment by removing, from the first segment, a first artifact corresponding to the chest compressions; generating a first shock index based on the first filtered segment, the first shock index corresponding to a certainty that the first filtered segment includes a shockable rhythm; and generating the first shock decision by comparing the first shock index to a first threshold and a second threshold, and wherein generating the second shock decision by analyzing the second segment of the ECG that corresponds to the second time window includes: generating a second filtered segment by removing, from the second segment, a second artifact corresponding to the chest compressions; generating a second shock index based on the second filtered segment, the second shock index corresponding to a certainty that the second filtered segment includes the shockable rhythm; and generating the second shock decision by comparing the second shock index to the first threshold and the second threshold.
6. The medical device of clause 4 or 5, wherein the first time window and the second time window occur during a single cardiopulmonary resuscitation (CPR) period.
7. The medical device of any one of clauses 4 to 6, wherein the second time window partially overlaps with the first time window.
8. The medical device of any one of clauses 4 to 7, wherein generating the second shock decision by analyzing the second segment of the ECG that corresponds to the second time window is in response to generating the first shock decision by analyzing the first segment of the ECG that corresponds to the first time window, the second time window being non-overlapping with the first time window.
9. The medical device of any one of clauses 4 to 8, wherein the first shock decision includes a shockable decision, and wherein the second shock decision includes a shockable decision, an indeterminate decision, or a nonshockable decision.
10. The medical device of any one of clauses 4 to 9, wherein generating the recommendation based on the second shock decision is independent of the first shock decision.
11. The medical device of any one of clauses 4 to 10, the input signal being a first input signal, the medical device further including: a discharge circuit configured to output a defibrillation shock to the individual, wherein the input device is configured to receive a second input signal, wherein the recommendation recommends administering the defibrillation shock to the individual, and wherein the operations further include: in response to the input device receiving the second input signal, causing the discharge circuit to output the defibrillation shock to the individual.
12. The medical device of any one of clauses 4 to 11, wherein the operations further include: generating a third shock decision by analyzing a third segment of the ECG that corresponds to a third time window, an end time of the third time window occurring after an end time of the second time window; updating the recommendation based on the third shock decision; and causing the output device to output the updated recommendation.
13. The medical device of any one of clauses 4 to 12, wherein the output device includes a display or a speaker.
14. A method performed by a medical device, the method including: generating a first shock decision by analyzing a first segment of an electrocardiogram (ECG) of an individual that corresponds to a first time window during which the individual is receiving chest compressions; generating a second shock decision by analyzing a second segment of the ECG that corresponds to a second time window during which the individual is receiving chest compressions, a start time of the second time window occurring after a start time of the first time window; receiving an input signal activating an analysis mode of the medical device; in response to receiving the input signal, outputting a recommendation indicating whether to administer a defibrillation shock to the individual based on the second shock decision.

15. The method of clause 14, wherein generating the first shock decision by analyzing the first segment of the ECG that corresponds to the first time window includes: generating a first filtered segment by removing, from the first segment, a first artifact corresponding to the chest compressions; generating a first shock index based on the first filtered segment, the first shock index corresponding to a certainty that the first filtered segment includes a shockable rhythm; and generating the first shock decision by comparing the first shock index to a first threshold and a second threshold, and wherein generating the second shock decision by analyzing the second segment of the ECG that corresponds to the second time window includes: generating a second filtered segment by removing, from the second segment, a second artifact corresponding to the chest compressions; generating a second shock index based on the second filtered segment, the second shock index corresponding to a certainty that the second filtered segment includes the shockable rhythm; and generating the second shock decision by comparing the second shock index to the first threshold and the second threshold.

16. The method of clause 14 or 15, wherein the first time window and the second time window occur during a single cardiopulmonary resuscitation (CPR) period.

17. The method of any one of clauses 4 to 16, wherein a start time of the second time window occurs before an end time of the first time window.

18. The method of any one of clauses 4 to 17, wherein generating the second shock decision is in response to generating the first shock decision.

19. The method of any one of clauses 4 to 18, wherein the first shock decision includes a shockable decision, and wherein the second shock decision includes a shockable decision, an indeterminate decision, or a non-shockable decision.

20. The method of any one of clauses 4 to 19, wherein the recommendation is independent of the first shock decision.

21. The method of any one of clauses 4 to 20, the input signal being a first input signal, the method further including: receiving a second input signal; and in response to receiving the second input signal, administering the defibrillation shock to the individual.

22. An external defibrillator, including: a detection circuit configured to detect an electrocardiogram (ECG) of an individual receiving chest compressions during a cardiopulmonary resuscitation (CPR) period; a display configured to output a recommendation indicating whether to administer a defibrillation shock to the individual and a certainty of the recommendation; an input device configured to receive an input signal; a discharge circuit configured to output a defibrillation shock to the individual; a processor; and memory storing instructions that, when executed by the processor, cause the processor to perform operations including: identifying multiple segments of the ECG, start times of the multiple segments being separated by a predetermined period; generating multiple shock decisions by determining whether the multiple segments include a shockable rhythm, each of the multiple shock decision corresponding to one of the multiple segments; updating the recommendation based on the multiple shock decisions; determining certainties of the multiple shock decisions by determining likelihoods that the multiple segments include the shockable rhythm; updating the recommendation based on the certainties; and based on the user input, causing the discharge circuit to output the defibrillation shock to the individual after the CPR period.

23. The external defibrillator of clause 22, wherein generating the multiple shock decisions by determining whether the multiple segments include the shockable rhythm includes: determining that a first segment of the ECG includes the shockable rhythm; generating a first shock decision based on determining that the first segment of the ECG includes the shockable rhythm; and determining whether a second segment of the ECG includes the shockable rhythm, a start time of the second segment occurring after the start time of the first segment; and generating a second shock decision based on determining whether the second segment of the ECG includes the shockable rhythm, and wherein updating the recommendation based on the multiple shock decisions includes: changing the recommendation from indicating the first shock decision to indicating the second shock decision.

24. The external defibrillator of clause 22 or 23, wherein determining the certainties of the multiple shock decisions by determining likelihoods that the multiple segments include the shockable rhythm includes determining an average of the likelihoods, and wherein updating the recommendation based on the certainties includes updating the recommendation based on the average of the likelihoods.

25. The external defibrillator of any one of clauses 22 to 24, wherein a particular shock decision includes a shockable decision, and wherein the input device receives the input signal after the recommendation is updated based on the particular shock decision.

26. A medical device, including: a detection circuit configured to detect an electrocardiogram (ECG) of an individual receiving chest compressions; an output device configured to output a recommendation indicating whether to administer a defibrillation shock to the individual; a processor; and memory storing instructions that, when executed by the processor, cause the processor to perform operations including: identifying a first segment of the ECG that corresponds to a first time period; generating a first shock decision by determining whether the first segment of the ECG includes a shockable rhythm; generating the recommendation based on the first shock decision; identifying a second segment of the ECG that corresponds to a second time period, a start time of the second time period occurring after a start time of the first time period; generating a second shock decision by determining whether the second segment of the ECG includes the shockable rhythm; and updating the recommendation based on the second shock decision.

27. The medical device of clause 26, wherein the output device includes a display or a speaker.

28. The medical device of clause 26 or 27, wherein generating the first shock decision by determining whether the first segment of the ECG includes the shockable rhythm includes: generating a first filtered segment by removing, from the first segment, a first artifact corresponding to the chest compressions; calculating a first shock index based on the first filtered segment, the first shock index corresponding to a likelihood that the first filtered segment includes the shockable rhythm; and comparing the first shock index to a first threshold and a second threshold, and wherein generating the second shock decision by determining whether the second segment of the ECG includes the shockable rhythm includes: generating a second filtered segment by removing, from the second segment, a second artifact corresponding to the chest compressions; calculating a second shock index based on the second filtered segment, the second filtered segment corresponding to a likelihood that the second filtered segment includes the shockable rhythm; and comparing the second shock index to the first threshold and the second threshold.

29. The medical device of any one of clauses 26 to 28, wherein determining whether the first segment of the ECG includes the shockable rhythm includes determining that the first segment of the ECG includes the shockable rhythm.

30. The medical device of any one of clauses 26 to 29, wherein an end time of the first time period occurs after the start time of the second time period.

31. The medical device of any one of clauses 26 to 30, wherein an end time of the first time period occurs before or simultaneously with the start time of the second time period.

32. The medical device of any one of clauses 26 to 31, wherein the first time period and the second time period occur during a single cardiopulmonary resuscitation (CPR) period.

33. The medical device of any one of clauses 26 to 32, wherein the operations further include: determining a certainty of the first shock decision; and determining a certainty of the second shock decision, wherein generating the recommendation is further based on the certainty of the first shock decision, and wherein updating the recommendation is further based on the certainty of the second shock decision.

34. The medical device of any one of clauses 26 to 33, further including: an input device configured to receive an input signal from a user; and a discharge circuit configured to administer the defibrillation shock to the individual, wherein the operations further include: in response to the input device receiving the input signal, causing the discharge circuit to administer the defibrillation shock to the individual.

35. A method performed by a medical device, the method including: detecting an electrocardiogram (ECG) of an individual receiving chest compressions; identifying a first segment of the ECG that corresponds to a first time period; generating a first shock decision by determining whether the first segment of the ECG includes a shockable rhythm; generating a recommendation based on the first shock decision; outputting the recommendation; identifying a second segment of the ECG that corresponds to a second time period, a start time of the second time period occurring after a start time of the first time period; generating a second shock decision by determining whether the second segment of the ECG includes the shockable rhythm; updating the recommendation based on the second shock decision; and outputting the updated recommendation.

36. The method of clause 35, wherein generating the first shock decision by determining whether the first segment of the ECG includes the shockable rhythm includes: generating a first filtered segment by removing, from the first segment, a first artifact corresponding to the chest compressions; calculating a first shock index based on the first filtered segment, the first shock index corresponding to a likelihood that the first filtered segment includes the shockable rhythm; and comparing the first shock index to a first threshold and a second threshold, and wherein generating the second shock decision by determining whether the second segment of the ECG includes the shockable rhythm includes: generating a second filtered segment by removing, from the second segment, a second artifact corresponding to the chest compressions; calculating a second shock index based on the second filtered segment, the second filtered segment corresponding to a likelihood that the second filtered segment includes the shockable rhythm; and comparing the second shock index to the first threshold and the second threshold.

37. The method of clause 35 or 36, wherein determining whether the first segment of the ECG includes the shockable rhythm includes determining that the first segment of the ECG includes the shockable rhythm.

38. The method of any one of clauses 35 to 37, wherein an end time of the first time period occurs after the start time of the second time period.

39. The method of any one of clauses 35 to 38, wherein an end time of the first time period occurs before or simultaneously with the start time of the second time period.

40. The method of any one of clauses 35 to 39, wherein the first time period and the second time period occur during a single cardiopulmonary resuscitation (CPR) period.

41. The method of any one of clauses 35 to 40, wherein the operations further include: determining a certainty of the first shock decision; and determining a certainty of the second shock decision, wherein generating the recommendation is further based on the certainty of the first shock decision, and wherein updating the recommendation is further based on the certainty of the second shock decision.

42. The method of any one of clauses 35 to 41, further including: receiving an input signal from a user; and in response receiving the input signal, administering the defibrillation shock to the individual.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing implementations of the disclosure in diverse forms thereof.

As will be understood by one of ordinary skill in the art, each implementation disclosed herein can comprise, consist essentially of or consist of its particular stated element, step, or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the implementation to the specified elements, steps, ingredients or components and to those that do not materially affect the implementation. As used herein, the term "based on" is equivalent to "based at least partly on," unless otherwise specified.

Unless otherwise indicated, all numbers expressing quantities, properties, conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing implementations (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate implementations of the disclosure and does not pose a limitation on the scope of the disclosure. No language in the specification should be construed as indicating any non-claimed element essential to the practice of implementations of the disclosure.

Groupings of alternative elements or implementations disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain implementations are described herein, including the best mode known to the inventors for carrying out implementations of the disclosure. Of course, variations on these described implementations will become apparent to those of ordinary skill in the art upon reading the foregoing description. The inventor expects skilled artisans to employ such variations as appropriate, and the inventors intend for implementations to be practiced otherwise than specifically described herein. Accordingly, the scope of this disclosure includes all modifications and equivalents of the subject matter recited in the claims appended hereto as permitted by applicable law. Moreover, any combination of the above-described elements in all possible variations thereof is encompassed by implementations of the disclosure unless otherwise indicated herein or otherwise clearly contradicted by context.

The invention claimed is:

1. A medical device, comprising:
   a detection circuit configured to detect an electrocardiogram (ECG) of an individual receiving chest compressions without a pause during a cardiopulmonary resuscitation (CPR) period;
   an input device configured to receive an input signal from a user;
   an output device configured to output a recommendation;
   a processor; and
   memory storing instructions that, when executed by the processor, cause the processor to perform operations comprising:
      generating a first shock decision by analyzing a first segment of the ECG that corresponds to a first time window in the CPR period;
      generating a second shock decision by analyzing a second segment of the ECG that corresponds to a second time window in the CPR period, a start time of the second time window occurring after a start time of the first time window;
      generating the recommendation indicating the second shock decision; and
      causing the output device to refrain from outputting the recommendation until the input device receives the input signal from the user.

2. The medical device of claim 1, wherein generating the first shock decision by analyzing the first segment of the ECG that corresponds to the first time window comprises:
   generating a first filtered segment by removing, from the first segment, a first artifact corresponding to the chest compressions;
   generating a first shock index by analyzing the first filtered segment, the first shock index corresponding to a certainty that the first filtered segment comprises a shockable rhythm; and
   generating the first shock decision by comparing the first shock index to a first threshold and a second threshold, and
   wherein generating the second shock decision by analyzing the second segment of the ECG that corresponds to the second time window comprises:
   generating a second filtered segment by removing, from the second segment, a second artifact corresponding to the chest compressions;
   generating a second shock index by analyzing the second filtered segment, the second shock index corresponding to a certainty that the second filtered segment comprises the shockable rhythm; and generating the second shock decision by comparing the second shock index to the first threshold and the second threshold.

3. The medical device of claim 1, wherein the second time window partially overlaps with the first time window.

4. The medical device of claim 1, wherein generating the second shock decision by analyzing the second segment of the ECG that corresponds to the second time window is in response to generating the first shock decision by analyzing the first segment of the ECG that corresponds to the first time window, the second time window being non-overlapping with the first time window.

5. The medical device of claim 1, wherein the first shock decision comprises a shockable decision, and
wherein the second shock decision comprises a shockable decision, an indeterminate decision, or a nonshockable decision.

6. The medical device of claim 1, wherein generating the recommendation indicating the second shock decision is independent of the first shock decision.

7. The medical device of claim 1, the input signal being a first input signal, the medical device further comprising:
a discharge circuit configured to output a defibrillation shock to the individual,
wherein the input device is configured to receive a second input signal,
wherein the recommendation recommends administering the defibrillation shock to the individual, and
wherein the operations further comprise:
in response to the input device receiving the second input signal, causing the discharge circuit to output the defibrillation shock to the individual.

8. The medical device of claim 1, wherein the operations further comprise:
generating a third shock decision by analyzing a third segment of the ECG that corresponds to a third time window, an end time of the third time window occurring after an end time of the second time window;
updating the recommendation indicating the third shock decision; and
causing the output device to output the updated recommendation.

9. The medical device of claim 1, wherein the output device comprises a display or a speaker.

10. The medical device of claim 1, wherein the input signal is received by the input device during the CPR period and after an end time of the second time window.

11. The medical device of claim 1, wherein the CPR period is longer than or equal to 30 seconds and shorter than or equal to three minutes.

12. The medical device of claim 1, wherein the output device is configured to output the recommendation within a delay period after the input device receives the input signal, and
wherein the first time window is longer than the delay period, and
wherein the second time window is longer than the delay period.

13. The medical device of claim 1, wherein the second shock decision is an indeterminate decision, and
wherein the recommendation comprises an instruction to pause administration of the chest compressions.

14. The medical device of claim 1, wherein the operations further comprise determining a start time of the second time window in the CPR period by analyzing a processing load on the processor.

15. The medical device of claim 2, wherein analyzing the first filtered segment comprises:
determining similarity between the first filtered segment and a shockable rhythm.

16. A method performed by a medical device, the method comprising:
detecting, by a detection circuit, an electrocardiogram (ECG) of an individual receiving chest compressions without a pause during a cardiopulmonary resuscitation (CPR) period;
generating, by a processor, a first shock decision by analyzing a first segment of the ECG that corresponds to a first time window in the CPR period;
generating, by the processor, a second shock decision by analyzing a second segment of the ECG that corresponds to a second time window in the CPR period, a start time of the second time window occurring after a start time of the first time window;
generating, by the processor, a recommendation indicating the second shock decision;
in response to generating the recommendation indicating the second shock decision, receiving, by an input device, an input signal; and
in response to receiving the input signal, outputting, by an output device, the recommendation.

17. The method of claim 16, wherein generating the first shock decision by analyzing the first segment of the ECG that corresponds to the first time window comprises:
generating a first filtered segment by removing, from the first segment, a first artifact corresponding to the chest compressions;
generating a first shock index by analyzing the first filtered segment, the first shock index corresponding to a certainty that the first filtered segment comprises a shockable rhythm; and
generating the first shock decision by comparing the first shock index to a first threshold and a second threshold, and
wherein generating the second shock decision by analyzing the second segment of the ECG that corresponds to the second time window comprises:
generating a second filtered segment by removing, from the second segment, a second artifact corresponding to the chest compressions;
generating a second shock index by analyzing the second filtered segment, the second shock index corresponding to a certainty that the second filtered segment comprises the shockable rhythm; and
generating the second shock decision by comparing the second shock index to the first threshold and the second threshold.

18. The method of claim 16, wherein a start time of the second time window occurs before an end time of the first time window.

19. The method of claim 16, further comprising:
the input signal being a first input signal, the method further comprising:
receiving a second input signal; and
in response to receiving the second input signal, administering an electrical shock to the individual.

20. A monitor-defibrillator, comprising:
a detection circuit configured to detect an electrocardiogram (ECG) of an individual receiving chest compressions without a pause during a cardiopulmonary resuscitation (CPR) period;
an input device configured to receive an input signal from a user;
an output device;
a processor; and
memory storing instructions that, when executed by the processor, cause the processor to perform operations comprising:
  generating a first shock decision by analyzing a first segment of the ECG that corresponds to a first time window in the CPR period;
  generating a first recommendation indicating the first shock decision;
  causing the output device to hide the first recommendation;
  generating a second shock decision by analyzing a second segment of the ECG that corresponds to a second time window in the CPR period, a start time of the second time window occurring after a start time of the first time window and occurring before an end time of the first time window, an end time of the second time window occurring before the input device receives the input signal from the user;
  generating a second recommendation indicating the second shock decision; and
  causing the output device to hide the second recommendation until the input device receives the input signal.

* * * * *